US011651837B2

(12) United States Patent
Noori et al.

(10) Patent No.: US 11,651,837 B2
(45) Date of Patent: May 16, 2023

(54) METHOD AND SYSTEM FOR DETERMINING A CONFORMATION OF A MOLECULE USING A HIGH-PERFORMANCE BINARY OPTIMIZER

(71) Applicant: 1QB INFORMATION TECHNOLOGIES INC., Vancouver (CA)

(72) Inventors: Moslem Noori, Vancouver (CA); Brad Woods, Vancouver (CA); Dominic Marchand, Vancouver (CA)

(73) Assignee: 1QB INFORMATION TECHNOLOGIES INC., Vancouver (CA)

( * ) Notice: Subject to any disclaimer, the term of this patent is extended or adjusted under 35 U.S.C. 154(b) by 794 days.

(21) Appl. No.: 16/671,767

(22) Filed: Nov. 1, 2019

(65) Prior Publication Data
US 2020/0143910 A1 May 7, 2020

Related U.S. Application Data

(60) Provisional application No. 62/754,919, filed on Nov. 2, 2018.

(51) Int. Cl.
*G16C 10/00* (2019.01)
*G06F 17/15* (2006.01)
(Continued)

(52) U.S. Cl.
CPC ............ *G16C 10/00* (2019.02); *G06F 17/15* (2013.01); *G16C 20/20* (2019.02); *G16C 20/50* (2019.02)

(58) Field of Classification Search
CPC combination set(s) only.
See application file for complete search history.

(56) References Cited

U.S. PATENT DOCUMENTS 8,244,504 B1 * 8/2012 Jacobs ............... G16B 15/00
703/22
8,374,828 B1 * 2/2013 Jacobs ............... G16B 15/20
703/2

(Continued)

OTHER PUBLICATIONS

Matsubara et al., "Ising-Model Optimizer with Parallel-Trial Bit-Sieve Engine," Complex, Intelligent, and Software Intensive Systems: Proceedings of the 11th International Conference on Complex, Intelligent, and Software Intensive Systems (CISIS-2017), pp. 432-438, 2018.

(Continued)

*Primary Examiner* — Michael Jung
(74) *Attorney, Agent, or Firm* — Pearl Cohen Zedek Latzer Baratz LLP

(57) ABSTRACT

A method is disclosed for determining a conformation of a molecule on at least one degree of freedom to optimize according to at least one molecular objective function, the method comprising generating using at least one corresponding degree of freedom to optimize a connected rigid bodies representation for the molecule by identifying a plurality of groups of atoms, generating a data structure representative of the connected rigid bodies representation generating at least one neighborhood for each generated neighborhood of the at least one generated neighborhoods, generating a corresponding binary optimization problem using the data structure, providing the generated corresponding binary optimization problem to a high-performance binary optimizer, obtaining a solution from the high-performance binary optimizer; and providing at least one corresponding solution.

18 Claims, 10 Drawing Sheets

(51) Int. Cl.
  *G16C 20/20* (2019.01)
  *G16C 20/50* (2019.01)

(56) References Cited

U.S. PATENT DOCUMENTS

2006/0225165 A1   10/2006  Massen Van Den Brink et al.
2016/0224515 A1*  8/2016   Ronagh .................. G06F 17/11

OTHER PUBLICATIONS

Farhi et al., "Quantum Adiabatic Evolution Algorithms versus Simulated Annealing," arXiv.org:quant ph/0201031 pp. 1-16, 2002.
McGeoch et al., "Experimental Evaluation of an Adiabatic Quantum System for Combinatorial Optimization," Computing Frontiers, Proceeding CF '13 Proceedings of the ACM International Conference on Computing Frontiers, Article No. 23, 11 pgs, May 14-16, 2013; http://www.cs.amherst.edu/ccm/cf14-mcgeoch.pdf.
Rappe et al., "UFF, a Full Periodic Table Force Field for Molecular Mechanics and Molecular Dynamics Simulations," J. Am. Chem. Soc., 1992, 114, 25, 10024-10035.

* cited by examiner

Original RB graph

Graph resulting from successive edge contractions

METHOD AND SYSTEM FOR DETERMINING A CONFORMATION OF A MOLECULE USING A HIGH-PERFORMANCE BINARY OPTIMIZER

CROSS-REFERENCE TO RELATED APPLICATION

The present application claims the benefit of U.S. Provisional Application No. 62/754,919, filed Nov. 2, 2018, which is incorporated herein in its entirety.

FIELD OF THE INVENTION

One or more embodiments of the invention relates to computers and chemistry. More precisely, one or more embodiments of the invention pertains to a method and system for determining a conformation of a molecule using a high-performance binary optimizer.

BACKGROUND OF THE INVENTION

Spatial geometry of a molecule is a determining factor in understanding molecular properties and chemical processes. A spatial arrangement of atoms within a molecule is often referred to as a conformation. The molecular energy of a conformation determines the probability of it occurring naturally. The problem of finding a set of high-quality conformations of a molecule, that have a favorable energy or that possess some desired features that can be expressed as an objective function, is referred to as conformational search problem. Solutions to the conformational search problem have many applications such as for instance in material design, in drug discovery, as well as in protein folding. Conformational analysis is the study of the energetics between different conformations.

Conformation search can also refer to the specific case of finding high-quality conformations of a molecule when only considering rotational degrees of freedom around single rotatable bonds. This is a special case related to conformational isomerism.

Computational techniques are increasingly exploited by chemical and pharmaceutical companies to expedite their research and development while saving on costly lab experiments. Such computational techniques are also considered for the conformational search problem. For this, a set of molecular degrees of freedom is chosen and the conformational search problem is computationally solved for the selected degrees of freedom. The size of the conformational search space, however, grows very quickly, often exponentially, with the number of selected degrees of freedom. Such an exploding search space makes it very difficult to solve the conformational search problem and requires the application of new methods as well as new computational paradigms.

The development of hardware and software to solve binary optimization problems is an intensely active area of research. High-performance binary optimizers (HPBO) are being developed that promise to solve binary problems much faster than traditional methods and algorithms that are available on traditional CPUs. Some optimizers are based on novel computing technologies like quantum computing and quantum annealing. Others are relying on highly parallel hardware implementation of known algorithms, or on clever combinations of specialized hardware and general-purpose hardware, firmware and software.

Currently developed high-performance binary optimizers have properties and limitations that need to be accounted for when devising new methods. Examples of limitations and properties include, inter alia, a connectivity and number of the registers or variables of the high-performance binary optimizer, bit precision of the parameters, type of binary functions that can be optimized, the ability to handle constraints or not, etc.

A large number of high-performance binary optimizers is limited to solving binary polynomial optimization problems of a fixed order.

A large number of high-performance binary optimizers is limited to solving quadratic unconstrained binary optimization (QUBO) problems. Examples include current quantum annealers, such as those developed by D-Wave Systems Inc. Other examples include digital annealers, such as those developed by Fujitsu which are based on hardware implementation of annealing algorithms.

The skilled addressee will appreciate that, unfortunately, very few problems are naturally formulated as quadratic unconstrained binary optimization or more generally as binary functions or binary polynomials optimization. Based on the properties and limitations of the high-performance binary optimizer, a choice of formulation may have a drastic impact on the performance. Being able to integrate and account for the specifics of the high-performance binary optimizer's properties is a highly non-trivial task and failure to devise a method with these limitations in mind will likely negate any potential advantage provided by the use of the high-performance binary optimizers.

There is a need for a method or system that can solve a conformational search problem while accounting for the limitations of the high-performance binary optimizer.

Features of one or more embodiments of the invention will be apparent from review of the disclosure, drawings and description of the one or more embodiments of the invention below.

BRIEF SUMMARY OF THE INVENTION

According to a broad aspect there is disclosed a computer-implemented method for determining a conformation of a molecule on at least one degree of freedom to optimize according to a molecular objective function using a high-performance binary optimizer characterized by at least one property, the method comprising providing an indication of a conformational search problem comprising an indication of a molecule comprising a plurality of atoms and at least one corresponding degree of freedom to optimize and a corresponding molecular objective function; generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize; generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize; generating at least one neighborhood using the generated data structure and the at least one property of the high-performance binary optimizer, wherein the generating of a given neighborhood comprises restricting at least one data of the second set of data of the data structure to at least one given value; for each generated neighborhood of the at least one generated neighborhoods: generating a corresponding binary optimization problem using the data structure having the at least one data of the second set of data restricted to the at least one given value and the corresponding molecular objective function, providing the generated corresponding binary optimization problem to the high-performance binary optimizer, obtaining at least one solution from the high-performance binary optimizer; and providing at least one corresponding solution.

In accordance with an embodiment, the molecular objective function comprises one of a molecular energy model and a molecular surface area.

In accordance with an embodiment, the at least one degree of freedom is selected from a group consisting of a torsional degrees of freedom.

In accordance with an embodiment, the data structure is a rigid bodies graph comprises a plurality of vertices and at least one edge, further wherein each data of the first set of data is a corresponding vertex of the plurality of vertices of the rigid bodies graph and each data of the second set of data is an edge of the at least one edge of the rigid bodies graph.

In accordance with an embodiment, a plurality of corresponding binary optimization problems are generated for each generated neighborhood, further wherein each of the plurality of corresponding binary optimization problems generated is provided to the high-performance binary optimizer, further wherein a plurality of corresponding solutions are obtained from the high-performance binary optimizer.

In accordance with an embodiment, the method further comprises selecting a solution amongst the plurality of corresponding solutions obtained for each neighborhood based on a criterion.

In accordance with an embodiment, the providing of a plurality of corresponding solutions comprises selecting at least one given solution based on a given criterion and providing the at least one selected solution.

In accordance with an embodiment, the indication of a conformational search problem further comprises at least one constraint associated with the conformational search problem, further wherein the at least one neighborhood is generated using the at least one constraint associated with the conformational search problem.

In accordance with an embodiment, the at least one constraint associated with the conformational search problem comprises a limitation on a value that a given degree of freedom to optimize may take.

In accordance with an embodiment, the value that a given degree of freedom to optimize may take is limited to one of at least one specific discrete value and a given range of values.

In accordance with an embodiment, the indication of the conformational search problem comprises more than one corresponding molecular objective function.

In accordance with an embodiment, the obtaining of the at least one solution from the high-performance binary optimizer comprises receiving more than one solution for the generated corresponding binary optimization problem.

In accordance with an embodiment, the method further comprises determining if a corresponding generated solution matches a criterion; further wherein the corresponding generated solution is discarded if it does not match the criterion.

In accordance with an embodiment, the criterion is selected from a group consisting of a maximum number of solutions to keep and a minimum corresponding quality for a solution defined according to the molecular objective function.

In accordance with an embodiment, the property of the high-performance binary optimizer comprises a maximum degree and connectivity of a binary polynomial optimization problem that can be solved by the high-performance binary optimizer.

In accordance with an embodiment, the high-performance binary optimizer is one of a quantum annealer and a digital annealer.

In accordance with a broad aspect, there is disclosed a non-transitory computer-readable storage medium for storing computer-executable instructions which, when executed, cause a processing device to perform a method for determining a conformation of a molecule on at least one degree of freedom to optimize according to a molecular objective function using a high-performance binary optimizer characterized by at least one property, the method comprising providing an indication of a conformational search problem comprising an indication of a molecule comprising a plurality of atoms and at least one corresponding degree of freedom to optimize and a corresponding molecular objective function; generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize; generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize; generating at least one neighborhood using the generated data structure and the at least one property of the high-performance binary optimizer, wherein the generating of a given neighborhood comprises restricting at least one data of the second set of data of the data structure to at least one given value; for each generated neighborhood of the at least one generated neighborhoods: generating a corresponding binary optimization problem using the data structure having the at least one data of the second set of data restricted to the at least one given value and the corresponding molecular objective function, providing the generated corresponding binary optimization problem to the high-performance binary optimizer, obtaining at least one solution from the high-performance binary optimizer; and providing at least one corresponding solution.

In accordance with a broad aspect, there is disclosed a digital computer comprising a central processing unit; a display device; a communication port for operatively connecting the digital computer to a high-performance binary optimizer characterized by at least one property; and a memory unit comprising an application for determining a conformation of a molecule on at least one degree of freedom to optimize according to a molecular objective function using the high-performance binary optimizer characterized by at least one property, the application comprising instructions for providing an indication of a conformational search problem comprising an indication of a molecule comprising a plurality of atoms and at least one corresponding degree of freedom to optimize and a corresponding molecular objective function; instructions for generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize; instructions for generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize; instructions for generating at least one neighborhood using the generated data structure and the at least one property of the high-performance binary optimizer, wherein the generating of a given neighborhood comprises restricting at least one data of the second set of data of the data structure to at least one given value; instructions for, for each generated neighborhood of the at least one generated neighborhoods: generating a corresponding binary optimization problem using the data structure having the at least one data of the second set of data restricted to the at least one given value and the corresponding molecular objective function, providing the generated corresponding binary optimization problem to the high-performance binary optimizer, and obtaining at least one solution from the high-performance binary optimizer; and instructions for providing at least one corresponding solution.

An advantage of one of more embodiments of the method disclosed is that it takes advantage of high-performance binary optimizers to solve conformational search problems while addressing the exponential computational complexity of the problem.

Another advantage of one of more embodiments of the method disclosed is that it enables promising quantum technologies, such as quantum annealing, to be harnessed for solving problems of increasing complexity that are not possible to be solved using traditional hardware on conventional CPUs.

Another advantage of one of more embodiments of the method disclosed is that it takes into account the limitations of high-performance binary optimizers and may be easily adapted to account for changing specifications and improvements of high-performance binary optimizers, thus providing a scalable method with evolving hardware.

Another advantage of one of more embodiments of the method disclosed is that it is flexible with the choice of degrees of freedom, molecular objective function, and possible restrictions to the values of the degrees of freedom to be optimized.

Another advantage of one of more embodiments of the method disclosed is that it may be combined with other solvers and methods for developing hybrid methods.

Another advantage of one of more embodiments of the method disclosed is that it may be used both for sampling high-quality conformations of the conformational search space and finding elite high-quality conformations.

BRIEF DESCRIPTION OF THE DRAWINGS

In order that the invention may be readily understood, embodiments of the invention are illustrated by way of example in the accompanying drawings.

DETAILED DESCRIPTION OF THE INVENTION

Figure 1:
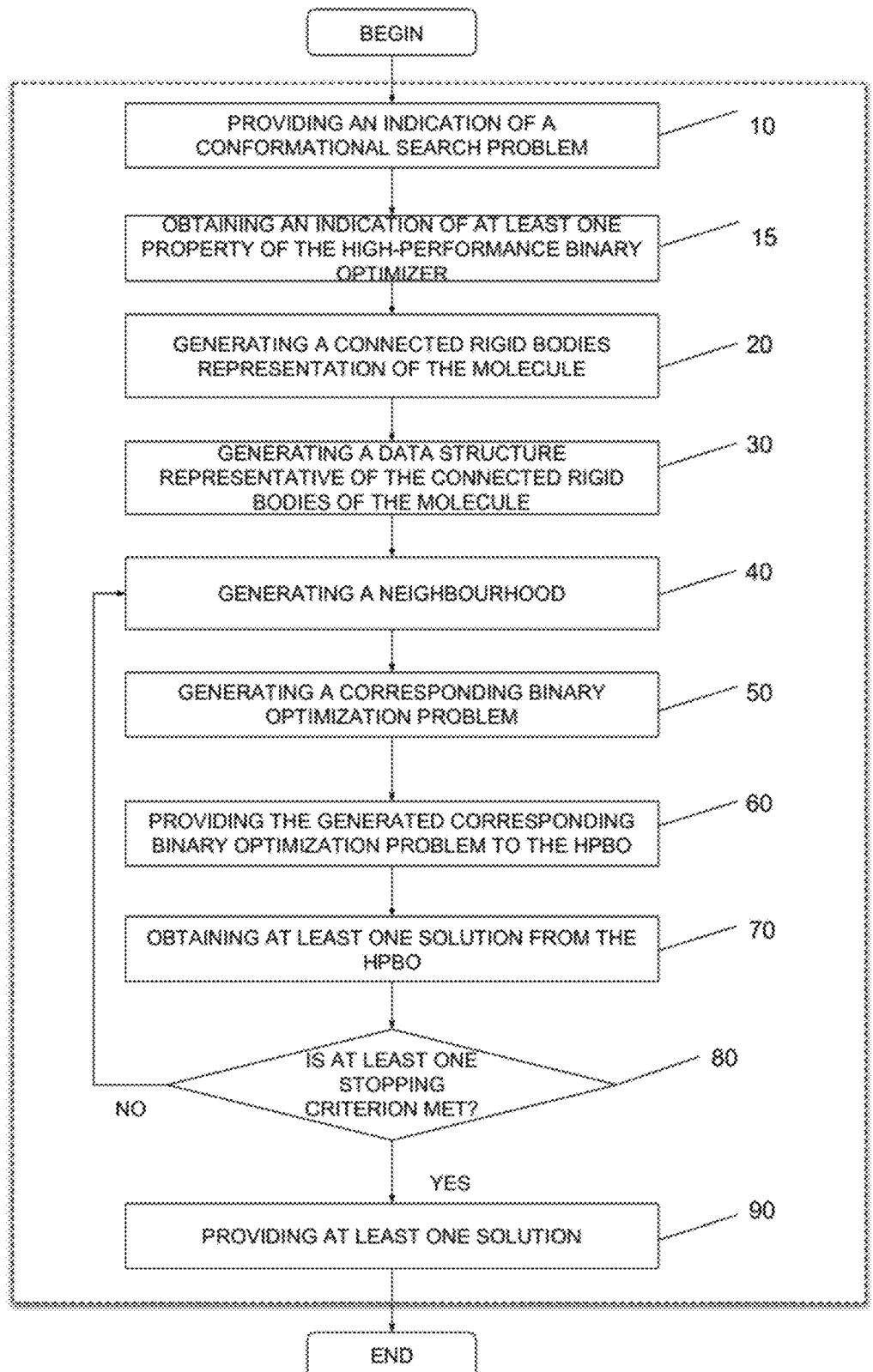
FIG. 1 is a flowchart which shows an embodiment of a method for determining a conformation of a molecule using a high-performance binary optimizer.

In the following description of the embodiments, references to the accompanying drawings are by way of illustration of an example by which the invention may be practiced.

Terms

The term "invention" and the like mean "the one or more inventions disclosed in this application," unless expressly specified otherwise.

The terms "an aspect," "an embodiment," "embodiment," "embodiments," "the embodiment," "the embodiments," "one or more embodiments," "some embodiments," "certain embodiments," "one embodiment," "another embodiment" and the like mean "one or more (but not all) embodiments of the disclosed invention(s)," unless expressly specified otherwise.

A reference to "another embodiment" or "another aspect" in describing an embodiment does not imply that the referenced embodiment is mutually exclusive with another embodiment (e.g., an embodiment described before the referenced embodiment), unless expressly specified otherwise.

The terms "including," "comprising" and variations thereof mean "including but not limited to," unless expressly specified otherwise.

The terms "a," "an" and "the" mean "one or more," unless expressly specified otherwise.

The term "plurality" means "two or more," unless expressly specified otherwise.

The term "herein" means "in the present application, including anything which may be incorporated by reference," unless expressly specified otherwise.

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The term "e.g." and like terms mean "for example," and thus do not limit the terms or phrases they explain. For example, in a sentence "the computer sends data (e.g., instructions, a data structure) over the Internet," the term "e.g." explains that "instructions" are an example of "data" that the computer may send over the Internet, and also explains that "a data structure" is an example of "data" that the computer may send over the Internet. However, both "instructions" and "a data structure" are merely examples of "data," and other things besides "instructions" and "a data structure" can be "data."

The term "i.e." and like terms mean "that is," and thus limit the terms or phrases they explain.

The term "high-performance binary optimizer" (HPBO) and like terms mean a method or system comprising one or many types of hardware, software and firmware that can find optimal or sub-optimal solutions to a binary optimization problem.

The term "high-performance" in high-performance binary optimizer refers to a method or system that is designed to use methods and systems beyond traditional methods and algorithms that are available on generic CPUs, such as methods relying on special integrated circuits or quantum annealing.

It will be characterized that a high-performance binary optimizer is characterized by the type of optimization problems it can solve. For instance, a specific high-performance binary optimizer may be designed to find solutions to unconstrained binary optimization problems only, while another high-performance binary optimizer may be designed to accept specific types of constrained binary optimization problems. A high-performance binary optimizer may be further limited in terms of the type of the binary problems it can accept. An example is a high-performance quadratic unconstrained binary optimizer that can only optimize quadratic unconstrained binary optimization (QUBO) problems.

The term "annealer" and like terms means a high-performance binary optimizer system composed of one or many types of hardware that relies on an annealing process to find optimal or sub-optimal solutions to a binary optimization problem. An example is a system consisting of digital computer embedding a binary quadratic programming problem, attached to a special-purpose annealer chip that carries out the optimization of a configuration of spins.

The term "digital annealer" and like terms means an annealer high-performance binary optimizer system in which the annealer chip carries out the optimization using a hardware implementation of the annealing process. An example is a system consisting of digital computer embedding a quadratic unconstrained binary optimization problem, attached to a special-purpose annealer chip that carries out the optimization of a configuration of spins in an effective Ising spin model using a hardware implementation of an algorithm such as simulated annealing. An embodiment of such analog computer is disclosed by Matsubara Satoshi et al. (2018), "Ising-Model Optimizer with Parallel-Trial Bit-Sieve Engine," Complex, Intelligent, and Software Intensive Systems: Proceedings of the 11th International Conference on Complex, Intelligent, and Software Intensive Systems (CISIS-2017), pp 432-438. It will be appreciated that the term "digital annealer" may be used to refer to a device that relies on annealing but does not rely on quantum annealing.

The term "quantum annealer" means an annealer high-performance binary optimizer system that relies on quantum annealing to find optimal or sub-optimal solutions to a binary polynomial optimization problem. An example of this is a system restricted to solving quadratic unconstrained binary optimization problems, consisting of a digital computer embedding a quadratic unconstrained binary optimization problem as an Ising spin model, attached to an analog computer that carries optimization of a configuration of spins in an Ising spin model using quantum annealing as described, for example, in Farhi, E. et al., "Quantum Adiabatic Evolution Algorithms versus Simulated Annealing" arXiv.org:quant-ph/0201031 (2002), pp 1-16. An embodiment of such analog computer is disclosed by McGeoch, Catherine C. and Cong Wang, (2013), "Experimental Evaluation of an Adiabatic Quantum System for Combinatorial Optimization," Computing Frontiers, May 14-16, 2013 (http://www.cs.amherst.edu/ccm/cf14-mcgeoch.pdf) and also disclosed in U.S. Patent Application Publication No. US2006/0225165. It will be appreciated that the "quantum annealer" may also be comprised of "classical components," such as a classical computer. Accordingly, a "quantum annealer" may be entirely analog or an analog-classical hybrid.

The term "register" and like terms mean a variable, or a unit of information, or data unit which is used to carry out a computation or optimization. An example of register for a quantum annealer is a qubit and a bit for a digital annealer.

Neither the Title nor the Abstract is to be taken as limiting in any way as the scope of the disclosed invention(s). The title of the present application and headings of sections provided in the present application are for convenience only, and are not to be taken as limiting the disclosure in any way.

Numerous embodiments are described in the present application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural and logical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

With all this in mind, one or more embodiments of the present invention is directed to a computer-implemented method, a non-transitory computer-readable storage medium and a system for determining a conformation of a molecule using a high-performance binary optimizer.

As illustrated below, it will be appreciated that various embodiments of the method may be provided.

Figure 2A:
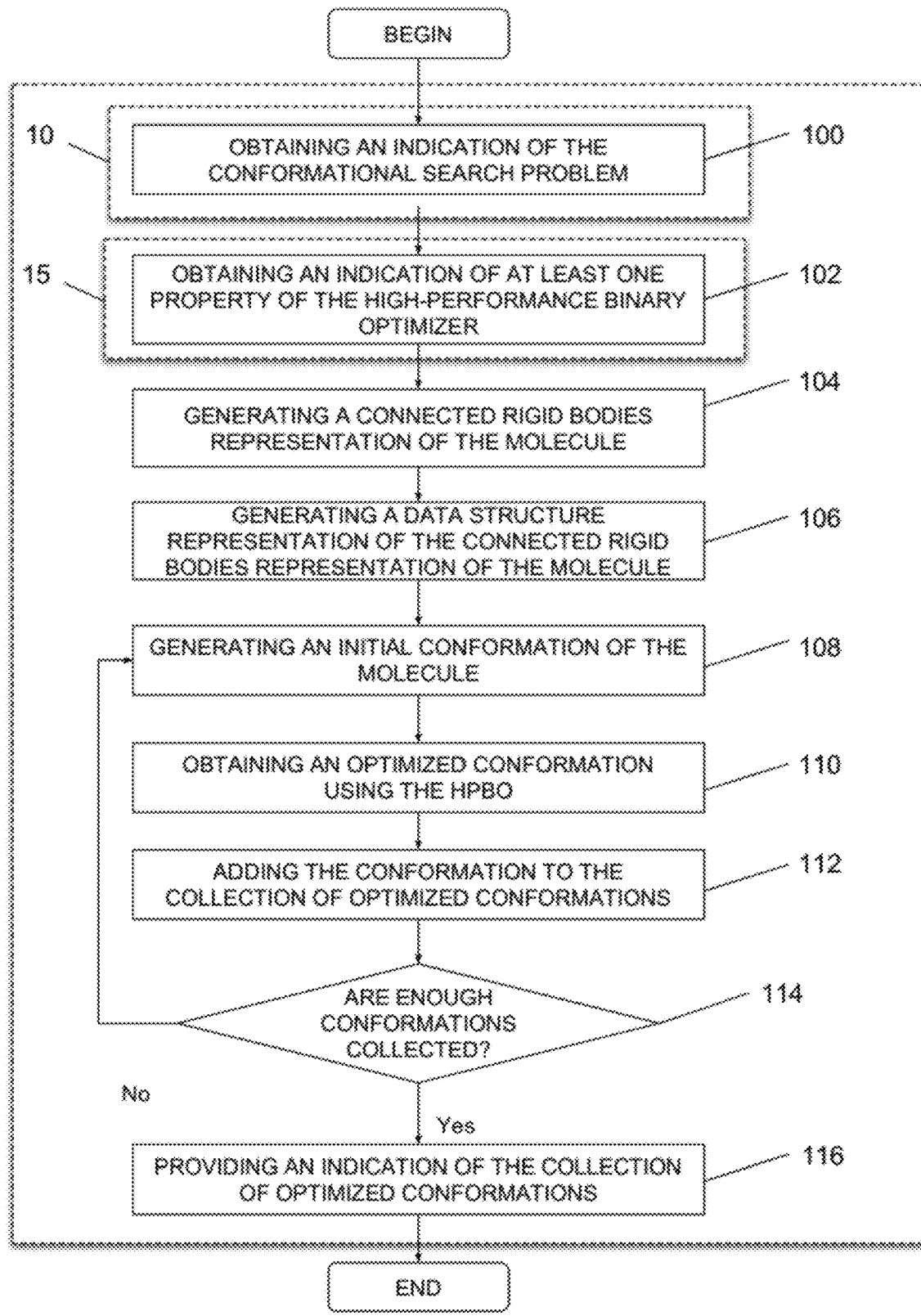
FIG. 2a is a flowchart which shows another embodiment of a method for determining a conformation of a molecule using the high-performance optimizer wherein a sampling of high-quality conformations of the molecule is performed using the high-performance binary optimizer.

Now referring to FIG. 2a, there is shown an embodiment of a method for sampling high-quality conformations of a molecule using a high-performance binary optimizer. In this embodiment, the sampling of high-quality conformations of the molecule is performed using the high-performance binary optimizer.

According to processing step 100, an indication of the conformational search problem is obtained.

It will be appreciated that the indication of the conformational search problem may be obtained according to various embodiments.

In one embodiment, the indication of the conformational search problem is obtained via a digital computer. In fact, it will be appreciated that in one embodiment, a digital computer is operatively connected to the high-performance binary optimizer. It will be appreciated that the connection between the digital computer and the high-performance binary optimizer may be of various types as known to the skilled addressee.

In one embodiment, the indication of the conformational search problem comprises an indication of a molecule comprising a plurality of atoms, at least one corresponding degree of freedom to optimize and at least one molecular objective function used for the optimization.

In one embodiment, the at least one molecular objective function comprises a molecular energy model. In another embodiment, the at least one molecular objective function comprises a molecular surface area. For example and in one embodiment, the surface area is considered only around the reaction site of the molecule.

It will be appreciated that in another embodiment, the indication of the conformational search problem further comprises at least one constraint associated with the at least one degree of freedom to optimize. It will be appreciated that the at least one constraint may comprise for instance a limitation on a value that a given degree of freedom may take. For instance and in one embodiment, the value is limited to at least one specific discrete value. In another embodiment, the value is restricted to a given range of values. The skilled addressee will appreciate that various alternative embodiments may be possible for the at least one constraint associated with the at least one degree of freedom to optimize.

Figure 3:
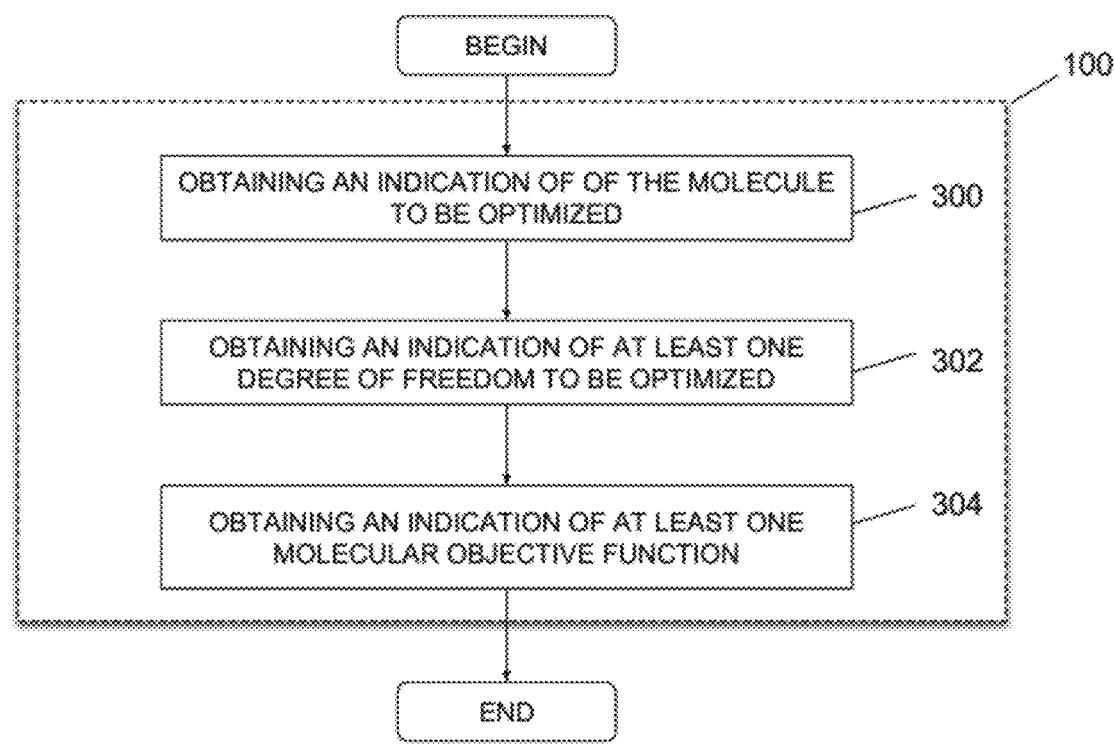
FIG. 3 is a flowchart which shows an embodiment for obtaining an indication of the conformational search problem.

Now referring to FIG. 3, there is shown an embodiment for obtaining an indication of the conformational search problem.

According to processing step 300, an indication of the molecule to be optimized is obtained.

In one embodiment, the indication of the molecule to be optimized comprises information about the atoms of the molecule, the bonds of the molecule, an initial spatial arrangement of the molecule and the various degrees of freedom of the molecule. The skilled addressee will appreciate that the information may be provided according to various embodiments.

In fact, it will be appreciated that in one embodiment, the indication of the molecule to be optimized comprises a molecular graph of the molecule with the atoms as vertices, the bonds of the molecule as edges and the properties as vertex and edge labels. In another embodiment, each vertex has properties that comprise an atom type and the corresponding three-dimensional coordinates of that atom in an initial spatial arrangement.

In accordance with another embodiment, the molecular graph is constructed by a user interacting with a digital computer.

In an alternative embodiment, the indication of the molecule to be optimized is obtained from another computer operatively connected to the digital computer. It will be appreciated by the skilled addressee that the indication of the molecule may be transmitted using various formats or media, such as standard file formats.

In another alternative embodiment, the indication of the molecule to be optimized is obtained from a software package or from a database stored or not in the digital computer.

It will be appreciated that the indication of the molecule to be optimized may be obtained according to various alternative embodiments and various components of that indication may be obtained separately or together according to similar or different embodiments.

It will be appreciated by the skilled addressee that the input spatial arrangement of the atoms in the molecule may define a baseline conformation of the molecule.

In one embodiment, the indication of the three-dimensional coordinates of the atoms is generated with at least one or a combination of various optimization methods and molecular energy models.

Still referring to FIG. 3 and according to processing step 302, an indication of at least one degree of freedom to be optimized is obtained. It will be appreciated by the skilled addressee that the at least one degree of freedom obtained may not necessarily comprise all the degrees of freedom of the molecule. It will be further appreciated by the skilled addressee that the selection of the at least one degree of freedom to be optimized may be obtained according to various embodiments.

It will be appreciated that in one embodiment, the conformational search is restricted to a subset of the atomic and molecular degrees of freedom.

Figure 7:
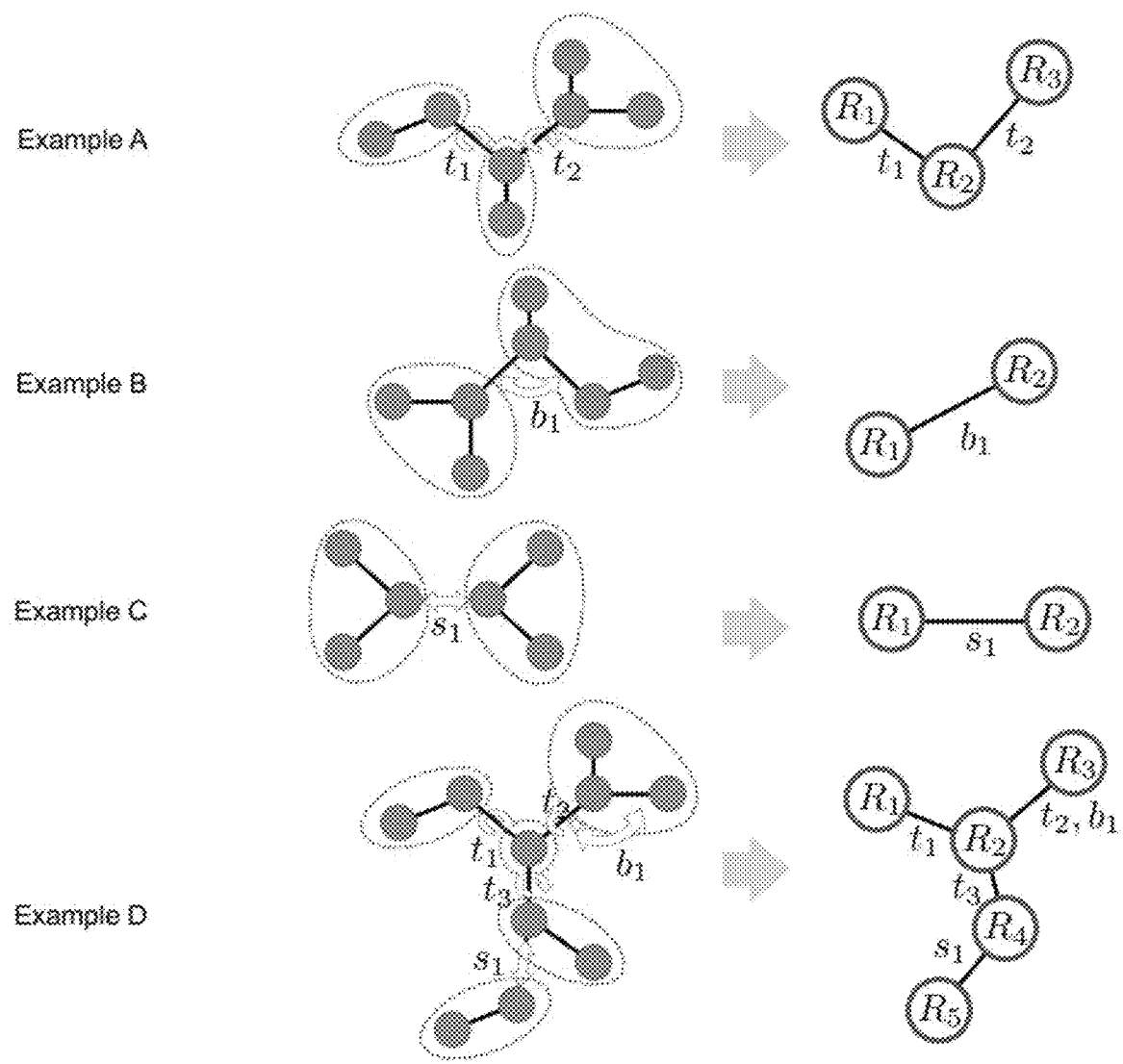
FIG. 7 is a diagram which illustrates embodiments of the construction of rigid bodies graph for various given molecular structures and degrees of freedom.

Now referring to the left-hand side of FIG. 7, there is shown some embodiments of molecular graphs and degrees of freedom including torsional, bending and bond-stretching degrees of freedom.

It will be appreciated that in accordance with another embodiment, the degrees of freedom selected are all, or a subset of, the torsional degrees of freedom associated with rotatable bonds of the molecule.

It will be appreciated that in accordance with another embodiment, the rotatable bonds are selected using a computer procedure based on the molecular graph of the molecule and the type of the bonds.

It will be appreciated that in accordance with an embodiment, the degrees of freedom to be optimized may be selected by a person skilled in the art, based for instance on previous knowledge, chemical intuition and experimental data.

It will be appreciated that such selection by a person skilled in the art may be performed based on a ranking of importance for various degrees of freedom. For instance, important degrees of freedom may be included while less important degrees of freedom may be ignored for a first approximation.

In one embodiment, the indication of at least one degree of freedom to be optimized comprises restrictions associated with individual degrees of freedom. It will be appreciated that restrictions may take various forms in different embodiments. It will further be appreciated that the restrictions to a degree of freedom may be obtained in various ways according to various embodiments.

In one embodiment, the restriction to a degree of freedom is specified as an allowed range of values.

In accordance with an alternative embodiment, the restriction to a degree of freedom is specified as part of a set of discrete values allowed. It will be appreciated that a specific choice for a discrete set of values may be referred to as a discretization grid. It will be appreciated that various choices for this set may be made according to various embodiments. It will further be appreciated that this grid does not need to be regular.

According to another alternative embodiment, no discretization grid is selected during this processing step and the full continuous range of the degree of freedom is allowed. According to another alternative embodiment, a restriction on the degree of freedom is provided as a continuous range.

Now referring back to FIG. 3 and according to processing step 304, an indication of at least one corresponding molecular objective function, or molecular energy model, is obtained. It will be appreciated by the skilled addressee that the energy model defines a type of objective function which is defined based on physical or chemical energy.

In one embodiment, the at least one molecular objective function is not exclusively based on physics and chemistry models for the energy of the molecule, but may comprise other objective function components based on desired properties of the conformations of the molecule. It will be appreciated that each of these other molecular objective functions addresses one of the molecular features. For example and in one embodiment, the molecular objective function is the surface area of at least one part of the molecule.

In one embodiment, other constraints and properties are included in the molecular objective function by adding corresponding extra reward or penalty terms.

In one embodiment, the at least one molecular objective function or energy model is selected by the user interacting with a digital computer. The selection may be made based on known accuracy limitations of different energy models for different molecules.

In one embodiment, the energy model is a general force field such as the universal force field described in "UFF, a Full Periodic Table Force Field for Molecular Mechanics and Molecular Dynamics Simulations," *J. Am. Chem. Soc.* 114 10024-10035 (1992)."

In an alternative embodiment, the energy model comprises a force field parametrized for the case of the molecule to be optimized or a family of molecules to which the molecule belongs.

Now referring back to FIG. 2a and according to processing step 102, an indication of at least one property of the high-performance binary optimizer is obtained.

It will be appreciated that in one embodiment, the digital computer is operatively connected to the high-performance binary optimizer and the indication of the at least one property of the high-performance binary optimizer is obtained directly through a query.

In an alternative embodiment, the indication of the at least one property of the high-performance binary optimizer is provided by the user interacting with the digital computer.

It will be appreciated that the at least one property of the high-performance binary optimizer may be of various types.

In one embodiment, the at least one property of the high-performance binary optimizer comprises a maximum degree of a binary polynomial optimization problem that can be solved by the high-performance binary optimizer.

In one embodiment, the at least one property of the high-performance binary optimizer comprises a number and a corresponding connectivity of the registers of the high-performance binary optimizer. It will be appreciated that the registers and their corresponding connectivity correspond to binary variables and their connectivity of the problems that can be handled by the high-performance binary optimizer. It will also be appreciated that a mapping between the variables of the binary optimization problems and the registers of the high-performance binary optimizer is required.

Still referring to FIG. 2a and according to processing step 104, a connected rigid bodies representation of the molecule is generated. It will be appreciated that the connected rigid bodies representation of the molecule is generated using the at least one corresponding degree of freedom to optimize.

In fact, it will be appreciated that the rigid bodies are defined by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize.

According to processing step 106, a data structure representative of the connected rigid bodies representation is generated. It will be appreciated that the data structure of the connected rigid bodies representation may be generated according to various embodiments.

It will be appreciated that the data structure representative of the connected rigid bodies representation illustrates a relationship between a first set of data and a second set of data. Each data of the first set of data corresponds to a given group of atoms of the connected rigid bodies representation and each data of the second set of data corresponds to a degree of freedom to optimize of the at least one degree of freedom to optimize.

In one embodiment, the generated data structure is a rigid bodies graph. The rigid bodies graph comprises a plurality of vertices and at least one edge. Each data of the first set of data is a corresponding vertex of the plurality of vertices of the rigid bodies graph and each data of the second set of data is an edge of the at least one edge of the rigid bodies graph. It will be appreciated that various information may be included with each vertex and edge based on various alternative embodiments.

Figure 4:
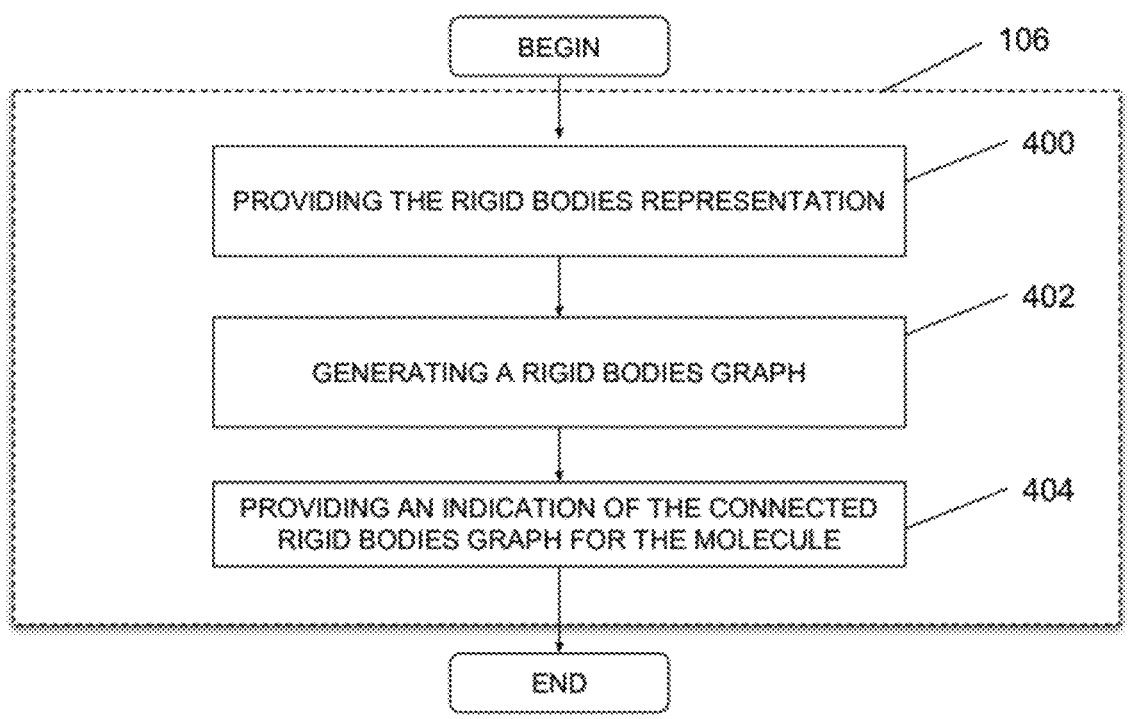
FIG. 4 is a flowchart which shows an embodiment for constructing a rigid bodies graph of the molecule.

Now referring to FIG. 4, there is shown an embodiment for generating the data structure representative of the connected rigid bodies representation. In this embodiment, the data structure is a rigid bodies graph comprising a plurality of vertices and at least one edge.

According to processing step 400, the connected rigid bodies representation is provided.

According to processing step 402, a rigid bodies graph is generated. It will be appreciated that the rigid bodies graph is generated by setting rigid bodies as vertices and bonds with degrees of freedom as edges.

It will be appreciated that the relative positions of atoms between two rigid bodies does not necessarily depend on all degrees of freedom. To identify which degrees of freedom will modify the relative positions of the atoms of two rigid bodies, the shortest path between the rigid bodies may be constructed and the edges on that path may be collected. The degrees of freedom attached to those edges form the subset of the degrees of freedom that will change the relative positions of the atoms within the rigid bodies considered.

Now referring to FIG. 7, there are shown various embodiments of molecular graphs and degrees of freedom and the corresponding rigid bodies graphs constructed from them.

Referring to example A, a rigid bodies graph of a molecule which consists of seven atoms and six bonds (including two torsional degrees of freedom t1 and t2) is generated. The rigid bodies graph with three vertices ($R_1$, $R_2$ and $R_3$) and two edges ($t_1$ and $t_2$) is generated.

Referring to example B, a rigid bodies graph of a molecule which consists of seven atoms and six bonds, two of which have bond bending degrees of freedom is generated. The rigid bodies graph with two vertices ($R_1$ and $R_2$) and one edge ($b_1$) is generated.

Referring to example C, a rigid bodies graph of a molecule which consists of six atoms and five bonds, one of which has a bond stretching degrees of freedom is generated. The rigid bodies graph with two vertices ($R_1$ and $R_2$) and one edge ($s_1$) is generated.

Referring to example D, a rigid bodies graph of a molecule which consists of ten atoms and nine bonds including three bonds with torsional degrees of freedom ($t_1$, $t_2$ and $t_3$), two bonds with bond bending degrees of freedom, and one bond with bond stretching degrees of freedom, is generated. The rigid bodies graph with five vertices ($R_1$, $R_2$, $R_3$, $R_4$ and $R_5$) and four edges is generated. The edge "$t_2,b_1$" combines two types of degrees of freedom, torsional and bond bending.

In one embodiment, interatomic energy computations among atoms from the same rigid body are independent from any degrees of freedom. The interaction energy for atoms within a rigid body may be computed once or simply be neglected to make the evaluation more efficient.

Now referring back to FIG. 4 and according to processing step 404, an indication of the rigid bodies graph of the molecule is provided.

In one embodiment, the degrees of freedom and their range of values are indicated as the labels for the edges of the rigid bodies graph.

In another embodiment, the coordinates of the atoms within a rigid body and the atom types are indicated as the labels of the nodes associated with the rigid body on the rigid bodies graph.

Now referring back to FIG. 2a and according to processing step 108, an initial conformation of the molecule is generated. This initial conformation of the molecule is used as a starting point for conformation optimization using the high-performance binary optimizer at processing step 110. It will be appreciated by the skilled addressee that an initial conformation of the molecule specifies the values of all the degrees of freedom that are being optimized. It will be appreciated that other degrees of freedom of the molecule that are not being optimized are not being set at this stage and may be obtained from the indication of the molecule obtained at processing step 300.

In one embodiment, the initial conformation of the molecule is represented by the values of the degrees of freedom associated with it.

In one embodiment, the three-dimensional coordinates of the atoms are computed based on the chosen values for each degree of freedom, stored temporarily, and are updated by the method as conformations of the molecule are created to enable the evaluation of the at least one objective function or molecular energy function.

In an alternative embodiment, given the values of the degrees of freedom, the three-dimensional coordinates of the atoms are only calculated when needed using the spatial arrangement of the atoms passed in processing step 300. It will be appreciated that only the values for the degrees of freedom are stored to represent this conformation of the molecule.

In one embodiment, an efficient calculation of the atom coordinates for different rigid bodies is done by preparing a transformation matrix associated with a specific degree of freedom that will transform the atom coordinates by multiplication. Finding the new relative coordinates of the atoms in a rigid body with respect to the atoms in another rigid body may be done by considering the multiplication of the transformation matrices of all degrees of freedoms (edges on the rigid bodies graph) lying on the path between the two rigid bodies.

In one embodiment, the degrees of freedom not being optimized are set based on the spatial arrangement of the atoms that was comprised in the indication of the molecule obtained at processing step 300.

It will be appreciated that the initial values for the degrees of freedom to be optimized for the initial conformation of the molecule may be obtained according to various embodiments.

In one embodiment, the initial conformation of the molecule is obtained randomly by sampling the allowed range or set of values for each degree of freedom.

In an alternative embodiment, the initial conformation of the molecule is obtained from another system or method for solving the conformational search method.

In yet another embodiment, the method and system disclosed herein are used in conjunction with another method by using the results of the method as an initial conformation of the molecule for the other method.

Figure 5:
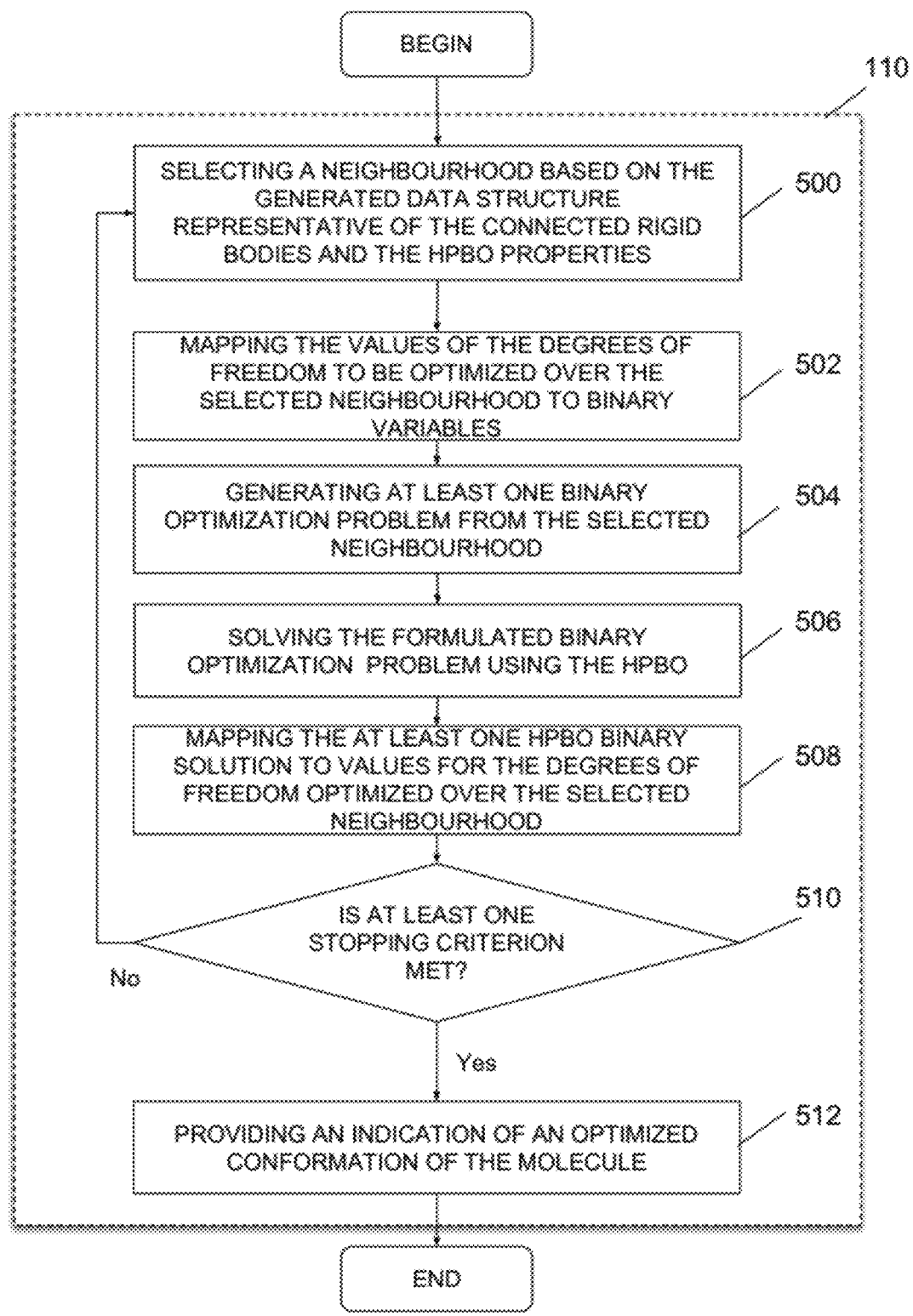
FIG. 5 is a flowchart which shows an embodiment for obtaining an optimized conformation of the molecule using the high-performance binary optimizer.

Now referring to FIG. 5, there is shown an embodiment for obtaining an optimized conformation of the molecule using the high-performance binary optimizer.

According to processing step 500, a neighborhood is selected in the conformational search space using the generated data structure representative of the connected rigid bodies and the at least one property of the high-performance binary optimizer. The neighborhood is selected for a partially optimized conformation of the molecule. It will be appreciated that this partially optimized conformation of the molecule is a copy of the initial conformation of the molecule generated at processing step 108 if this is the first time that processing step 500 is reached after processing step 108. Otherwise, it is the conformation of the molecule obtained at the end of processing step 508, when at least one stopping criterion is not met at processing step 510.

In a related embodiment, the neighborhood identifies a search space, over the degrees of freedom, which is explored by the high-performance binary optimizer at processing step 506.

In yet another related embodiment, the neighborhood is selected by fixing some of the degrees of freedom to their corresponding values in the partially optimized conformation of the molecule.

It will be appreciated that in one embodiment, when the generated data structure is a rigid bodies graph, the neighborhood selection is based on a connected graph minor of the rigid bodies graph.

Figure 6:
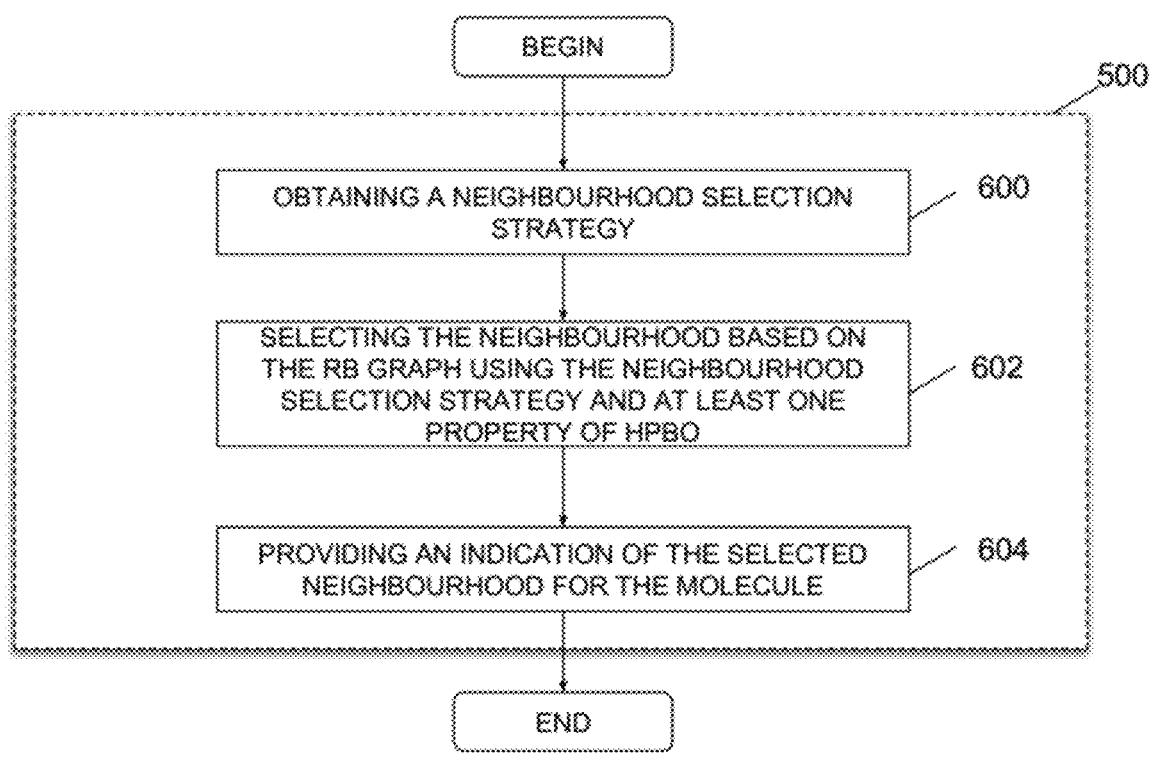
FIG. 6 is a flowchart which shows an embodiment for selecting a neighborhood based on the rigid bodies graph for the high-performance binary optimizer.

Now referring to FIG. 6, there is shown an embodiment for selecting a neighborhood based on the rigid bodies graph and the at least one property of the high-performance binary optimizer.

According to processing step 600, a neighborhood selection strategy is obtained. It will be appreciated that the neighborhood selection strategy may be obtained according to various embodiments.

Figure 8:
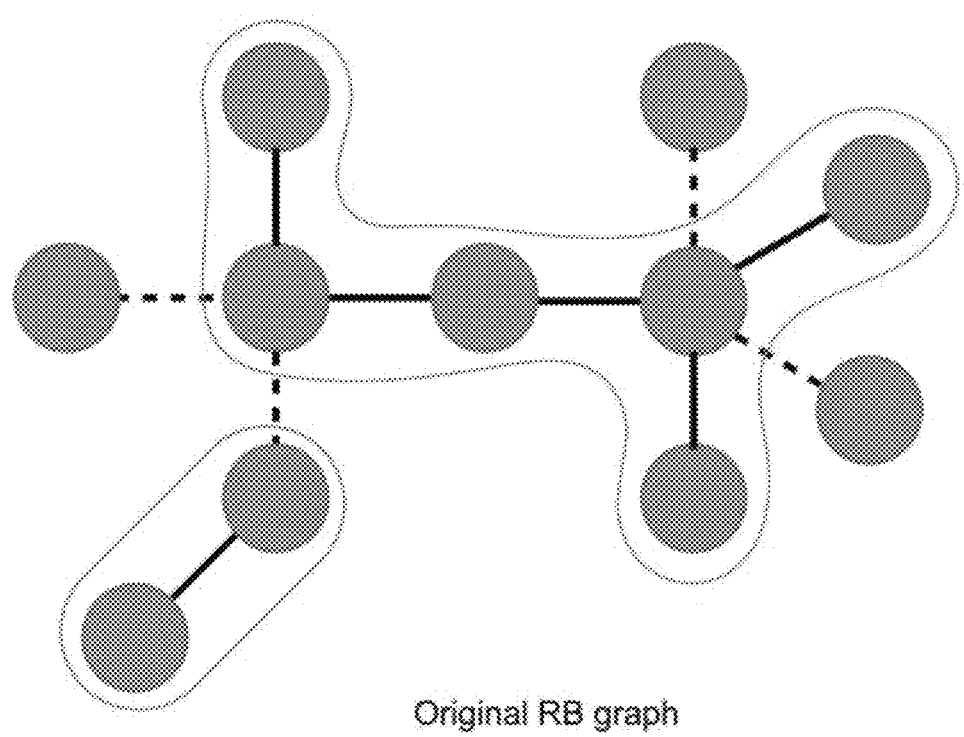
FIG. 8 is a diagram which illustrates one embodiment of the successive edge contraction.
Figure 8:
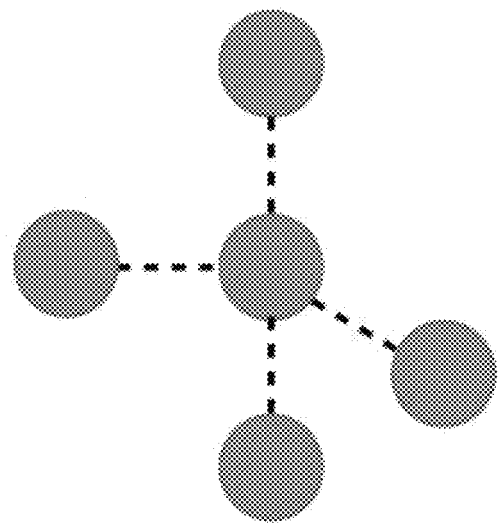

In one embodiment, the neighborhood selection strategy outlines how some edges of the rigid bodies graph are contracted resulting in a graph minor of the rigid body graph. An embodiment of the result of this edge contraction is disclosed at FIG. 8.

In another embodiment, the selection of edges for contraction is based on a prioritization of the degrees of freedom explicitly obtained at processing step 302.

In another embodiment, the order of the edge contraction is determined dynamically for example according to the initial conformation of the molecule generated at processing step 108 or according to the partially optimized conformations of the molecule derived at processing step 508.

Still referring to FIG. 6 and according to processing step 602, a neighborhood of the partially optimized conformation of the molecule is selected using the rigid bodies graph, the neighborhood selection strategy and the at least one property of the high-performance binary optimizer.

In one embodiment, wherein the maximum degree of the polynomial that can be solved by the high-performance binary optimizer is m, a connected graph minor of the rigid body graph with m-edge dependency is first selected to choose a neighborhood defined by the degrees of freedom to be optimized. The m-edge dependency means that the length of the shortest path between any two vertices of the selected minor graph is at most m. The number of m-edge dependent minors of the rigid bodies graph depends on the rigid bodies graph itself as well as the value of m. An arbitrary m-edge dependent minor of the rigid bodies graph, indexed by i, is denoted by $G_i=(V_i, E_i)$ where $V_i$ and $E_i$ respectively represent the set of vertices and edges of $G_i$. Also, the set of the degrees of freedom associated with $E_i$ is denoted by $\mathcal{T}$. Having a minor graph $G_i$, the neighborhood of the partially optimized conformation of the molecule is defined as all conformations of the molecule where the values of the molecular degrees of freedom to be optimized for these conformations of the molecule are equal to those for the partially optimized conformation of the molecule, except for the degrees of freedom in $\mathcal{T}$. This means that the degrees of freedom not in $\mathcal{T}$ are fixed to their corresponding values in the partially optimized conformation of the molecule.

In another embodiment, the neighborhood is restricted by constraints on the corresponding degrees of freedom to optimize. Such constraints restrict the values of the degrees of freedom in $\mathcal{T}$ in the selected neighborhood.

In another embodiment, the neighborhood selection comprises a restriction done by limiting the allowed values of a degree of freedom based on at least one property of the high-performance binary optimizer. For example, each degree of freedom which is not fixed may be restricted to only a subset of its allowed values so that the total number of variables in the corresponding binary optimization problem is compatible with the number of registers of the high-performance binary optimizer.

In another embodiment, the number of values that the degrees of freedom in $\mathcal{T}$ accept in the neighborhood is chosen according to the size of the binary optimization problem that can be solved by the high-performance binary optimizer.

According to processing step 604, an indication of the selected neighborhood for the molecule is provided. It will be appreciated that the selected neighborhood is the result of a combination of fixing and restricting different degrees of freedom.

In one embodiment, the indication of the selected neighborhood comprises a data structure illustrating the relation between the degrees of freedom and their corresponding values in the neighborhood.

Now referring back to FIG. 5 and according to processing step 502, the values of the degrees of freedom to be optimized over the selected neighborhood are mapped to binary variables. It will be appreciated that the mapping of the values of the degrees of freedom to be optimized over the selected neighborhood may be mapped to binary variables according to various embodiments.

In an embodiment, a one-hot encoding is employed to map the values of the degrees of freedom to be optimized over the selected neighborhood to binary variables.

In another embodiment, a binary encoding, i.e., representation in base 2, is used to map the values of the degrees of freedom to be optimized over the selected neighborhood to binary variables.

According to processing step 504, at least one binary optimization problem is generated. It will be appreciated that the at least one binary optimization problem is generated in order to find an optimal conformation of the molecule over the neighborhood selected at processing step 500.

In one embodiment, a binary optimization problem is generated for each of the at least one molecular objective function obtained at processing step 304. It will be appreciated by the skilled addressee that a solution obtained from the high-performance binary optimizer for each binary optimization problem is mapped to an optimal or sub-optimal conformation of the molecule for the corresponding molecular objective function over the selected neighborhood. In a related embodiment, some of the constraints over the conformational search problem obtained at processing step 100 are incorporated in the formulated binary optimization problems.

When the data structure representative of the connected rigid bodies is a rigid bodies graph, it will be appreciated that from the selected neighborhood, a binary optimization problem may be formulated to optimize the molecular objective function or the energy function obtained at processing step 304 with respect to the degrees of freedom indicated by the edges of the selected graph minor $G_i$ associated with the neighborhood.

In one embodiment, when the neighborhood is selected based on a minor graph $G_i$ of the rigid bodies graph and the molecular objective function is molecular energy, the binary optimization problem to find the best conformation of the molecule over the selected neighborhood may be formulated as:

$$\min \sum_{\substack{u,v \in V_i \\ u \neq v}} \sum_{k_1=1}^{d_{e_1}} \ldots \sum_{k_{p(u,v)}=1}^{d_{e_{p(u,v)}}} U_{uv}(t_{e_1} = \theta_{k_1}, \ldots, t_{e_{p(u,v)}} = \theta_{k_{p(u,v)}}) \prod_{j=1}^{p(u,v)} x_{e_j k_j} + p \sum_{e \in E_i} \left( \sum_{k=1}^{d_e} x_{ek} - 1 \right)^2$$

wherein p(u,v) is the length of the shortest path between nodes u and v of the selected minor graph $G_i$. Further, $(e_1, e_2, \ldots, e_{p(u,v)})$ refers to the sequence of the edges on the shortest path from u to v while $d_{e_j}$ and $d_e$ respectively refer to the number of values that are selected in the neighborhood for the degrees of freedom associated with e and e. In the above formulation, $U_{u,v}(\bullet)$ refers to the interaction energy of the two nodes u and v. Also, $t_{e_j}$ is the variable representing the degree of freedom associated with edge $e_j$ and $\theta_{k_j}$ is the $k_j$th value that $t_{e_j}$ takes. In addition, $x_{e_j k_j}$ is the binary variable associated with the $k_j$th value of $t_{e_j}$ and p is a large enough penalty value to enforce the one-hot encoding constraints by making sure each of $t_{e_j}$'s can take one and only one value in the solution of the above optimization problem.

According to processing step 506, the formulated binary optimization problem is solved using the high-performance binary optimizer. It will be appreciated that at least one solution is obtained from the high-performance binary optimizer for the formulated binary optimization problem.

In one embodiment, when the solution of the high-performance binary optimizer to the formulated binary optimization problem is not deterministic, for example with a quantum annealer or a Fujitsu Digital Annealer, a plurality of solutions may be obtained in order to increase the chances of finding a globally optimal solution over the selected neighborhood. In a related embodiment, the plurality of solutions is filtered to select one solution.

In one embodiment, when a plurality of binary optimization problems are formulated for a plurality of objective functions, the solutions are combined, to achieve a high-level of fitness, or quality, across all molecular objective functions, before updating the partially optimized conformation of the molecule.

According to processing step 508, the at least one binary solution obtained from the high-performance binary optimizer is mapped to values for the degrees of freedom to be optimized over the selected neighborhood.

In one embodiment, the at least one binary solution obtained from the high-performance binary optimizer is mapped to a set of corresponding values for the degrees of freedom to be optimized over the neighborhood as identified at processing step 500. Then, the partially optimized conformation of the molecule is updated by replacing its values for the degrees of freedom not fixed at processing step 500 by the ones obtained through mapping the at least one solution of the high-performance binary optimizer. In a related embodiment, the mapping of the binary solution to values for the degrees of freedom is done based on the one-hot encoding used at processing step 502.

In one embodiment, the plurality of solutions obtained from the high-performance binary optimizer are combined in a list that can be filtered according to at least one criterion before being mapped back to the values of the degrees of freedom and the corresponding conformations of the molecule.

According to processing step 510, a check is performed in order to find out if at least one stopping criterion is met. If at least one stopping criterion is met and according to processing step 512, an indication of an optimized conformation is provided. If this is not the case, the search for an optimized conformation of the molecule continues using the high-performance binary optimizer by repeating processing steps 500, 502, 504, 506, and 508.

It will be appreciated that the at least one stopping criterion may be of various types.

In one embodiment, a stopping criterion is defined as a maximum computational time to spend to find an optimized conformation of the molecule.

In another embodiment, a stopping criterion may be defined based on observing negligible improvement, in terms of the objective or energy function, in the partially optimized conformation after a certain number of iterations through processing steps 500, 502, 504, 506, and 508.

In yet another embodiment, a stopping criterion is defined based on reaching a target value for the objective or energy function in the partially optimized conformation of the molecule.

The skilled addressee will appreciate that various alternative embodiments may be provided for the stopping criterion.

Still referring to FIG. 5 and according to processing step 512, an indication of the optimized conformation of the molecule is provided.

In one embodiment, the optimized conformation of the molecule is a copy of the last partially optimized conformation of the molecule generated before reaching processing step 512.

Now referring back to FIG. 2a and according to processing step 112, the conformation of the molecule obtained with the processing step 110 is added to the collection of optimized conformations of the molecule.

In one embodiment, a check is performed before adding a conformation of the molecule to the collection of optimized conformations of the molecule based on at least one criterion provided by the user.

In one embodiment, the check is performed in order to avoid for instance collecting multiple copies of the same conformations of the molecule or conformations of the molecule that are too similar.

According to processing step 114, a test is performed on the size of the collection of optimized conformations of the molecule.

In the case where the size of the collection of optimized conformations of the molecule is not sufficient, at least one additional conformation of the molecule is generated by repeating processing steps 108 and 110

In the case where the size of the collection of optimized conformations of the molecule is sufficient and according to processing 116, an indication of the collection of optimized conformations of the molecule is provided.

Figure 2B:
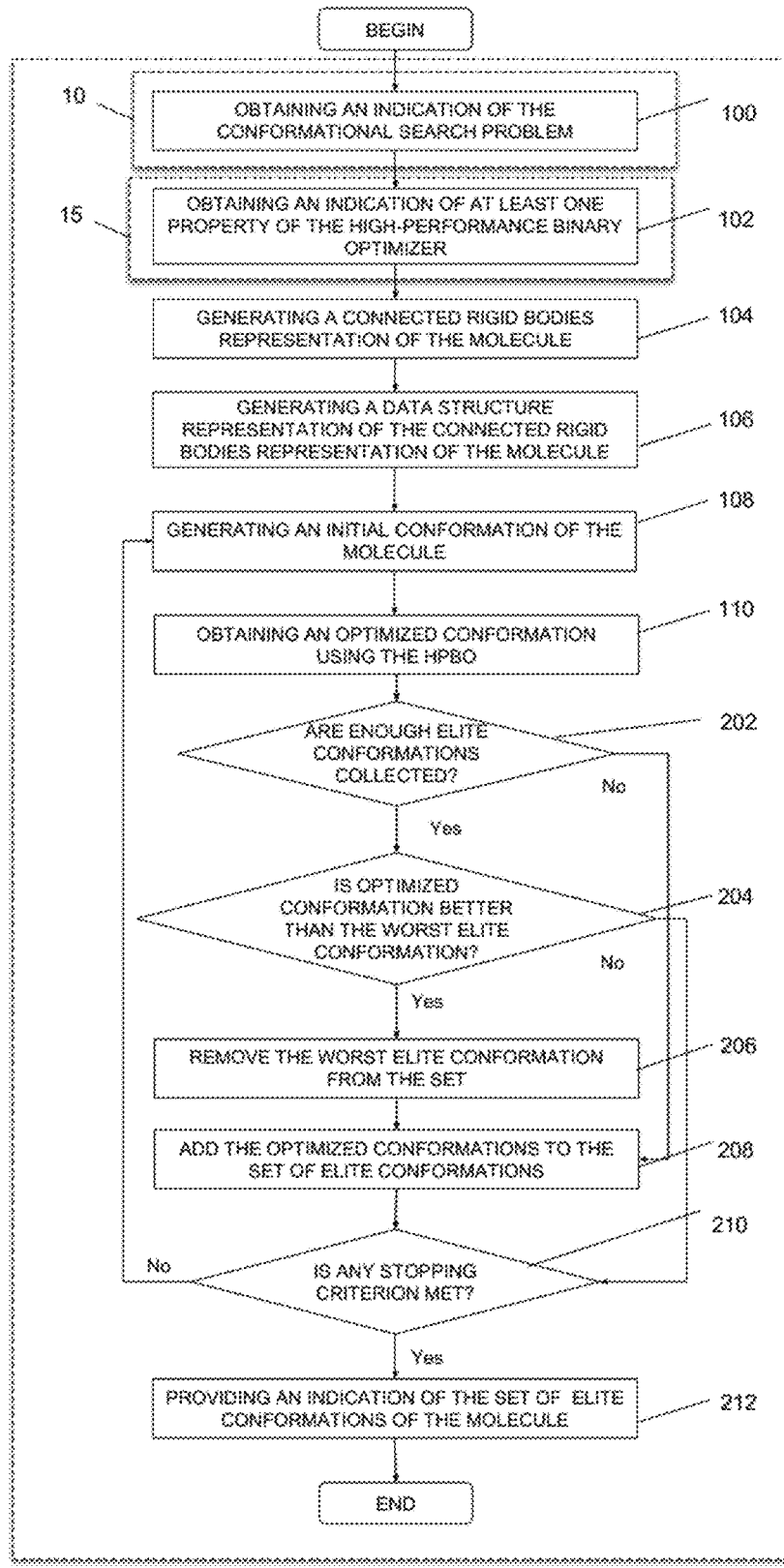
FIG. 2b is a flowchart which shows another embodiment of a method for determining a conformation of a molecule using the high-performance optimizer wherein elite high-quality conformations of a molecule are found using the high-performance binary optimizer.

Now referring to FIG. 2b, there is disclosed another embodiment of a method for determining a conformation of a molecule using the high-performance optimizer wherein elite high-quality conformations of a molecule are found using a high-performance binary optimizer.

It will be appreciated that an elite conformation of the molecule can be referred to as a high-quality conformation of the molecule, measured by at least one molecular objective function that was found to be of better quality than others. A group of elite conformations is the group of best conformations found. If a molecular energy model is used for the objective function, an elite conformation of the molecule is a low-energy conformation.

It will be appreciated that processing steps 100, 102, 104, 106, 108, 110, 112 remain unchanged from the corresponding processing steps disclosed in FIG. 2a.

According to processing step 202, a test is performed in order to find out if the size of the collection of found elite conformations of the molecule reaches a given size. In the case where the size of the collection of found elite conformations of the molecule reaches a certain size and according to processing step 204, a test is performed in order to find out if the optimized conformations of the molecule are better than the worst elite conformations of the molecule. In the case where the size of the collection of found elite conformations of the molecule does not reach a given size, processing step 208 is performed.

It will be appreciated that according to processing step 204, the optimized conformation of the molecule found in processing step 110 is compared with the already collected elite conformations of the molecule. If the new optimized conformation of the molecule is better than the worst elite conformation of the molecule already in the list, processing step 206 is performed. Otherwise, processing step 210 is performed. It will be appreciated by the skilled addressee that the quality of conformation and the comparison is based on the at least one molecular objective function.

In another embodiment, the comparison between the optimized conformation of the molecule and the worst elite conformation of the molecule is done based on the at least one objective function obtained at processing step 304.

In another embodiment, the comparison between the optimized conformation of the molecule and the worst elite confirmation of the molecule is done based on the energy function obtained at processing step 304.

According to processing step 206, the worst conformation of the molecule from the collection of elite conformations is removed. It will be appreciated that this is performed in order to make space for adding the optimized conformation of the molecule found at processing step 110.

In one embodiment, before removing the worst elite conformation of the molecule, molecular similarity between the optimized conformation of the molecule and the ones in the collection of elite conformations of the molecule is checked. If the optimized conformation of the molecule is not similar to any of them, or if it is similar to the worst conformation of the molecule, the worst elite conformation of the molecule is removed from the collection of elite conformations of the molecule.

The optimized conformation of the molecule found at processing step 110 is added to the collection of elite conformations of the molecule at processing step 208.

According to processing step 210, a check is performed to find out if at least one stopping criterion is met. In the case where at least one stopping criterion is met and according to processing step 212, an indication of the set of elite conformations of the molecule is provided. It will be appreciated that the search for elite conformations of the molecule will continue with processing steps 108, 110, 202, 204, 206 and 208 if the at least one stopping criterion is not met. It will be appreciated by the skilled addressee that the at least one stopping criterion may be of various types.

In one embodiment, the at least one stopping criterion of processing step 210 is defined in terms of a maximum computational time to spend for finding the collection of elite conformations of the molecule.

In another embodiment, the at least one stopping criterion of processing step 210 is defined based on a conformational diversity of the found collection of elite conformations of the molecule.

In a related embodiment, the at least one stopping criterion of processing step 210 is defined as a given number of iterations through the processing steps 108, 110, 202, 204, 206, and 208 with no added elite conformation to the collection.

Still referring to FIG. 2b and according to processing step 212, an indication of the found collection of elite conformations of the molecule is provided.

It will be appreciated that the embodiments disclosed in FIGS. 2a and 2b are specific embodiments of a method for determining a conformation of the molecule using the high-performance binary optimizer embodiment disclosed in FIG. 1.

Now referring to FIG. 1 and according to processing step 10, an indication of a conformational search problem is provided. It will be appreciated that in one embodiment this processing step is performed as processing step 100.

According to processing step 15, an indication of at least one property of the high-performance binary optimizer is obtained. It will be appreciated that in one embodiment this processing step is performed as processing step 102 disclosed above.

According to processing step 20, a connected rigid bodies representation of the molecule is generated. It will be appreciated that in one embodiment this processing step is performed as processing step 104 disclosed above.

According to processing step 30, a data structure representative of the connected rigid bodies of the molecule is generated. It will be appreciated that in one embodiment this processing step is performed as processing step 106 disclosed above.

According to processing step 40, at least one neighborhood is generated. It will be appreciated that in one embodiment this processing step is performed as processing step 500 disclosed above.

According to processing step 50, a corresponding binary optimization problem is generated. It will be appreciated that in one embodiment this processing step is performed as processing step 504 disclosed above.

According to processing step 60, the generated corresponding binary optimization problem is provided to the high-performance binary optimizer. It will be appreciated that this processing step may be performed according to various embodiments which are clear in view of the above disclosure.

According to processing step 70, at least one solution is obtained from the high-performance binary optimizer. It will be appreciated that this processing step may be performed according to various embodiments which are clear in view of the above disclosure.

According to processing step 80, a test is performed to find out if at least one stopping criterion is met. If the at least one stopping criterion is not met and according to processing step 40, another neighborhood is generated and the method continue with processing steps 50, 60 and 80. It will be appreciated that this processing step may be performed according to various embodiments which are clear in view of the above disclosure.

In the case where a criterion is met and according to processing step 90, at least one solution is provided. It will be appreciated that this processing step may be performed according to various embodiments which are clear in view of the above disclosure.

Applications

There is now disclosed an embodiment for solving a conformational search problem with a high-performance binary optimizer that can solve quadratic unconstrained binary optimization (QUBO) problems such as those that are currently available. It will be appreciated that two embodiments are considered for this application. In a first embodiment, the high-performance binary optimizer comprises a Fujitsu digital annealer while in a second embodiment, the high-performance binary optimizer comprises a quantum annealer. Both embodiments are disclosed hereinbelow.

Figure 9:
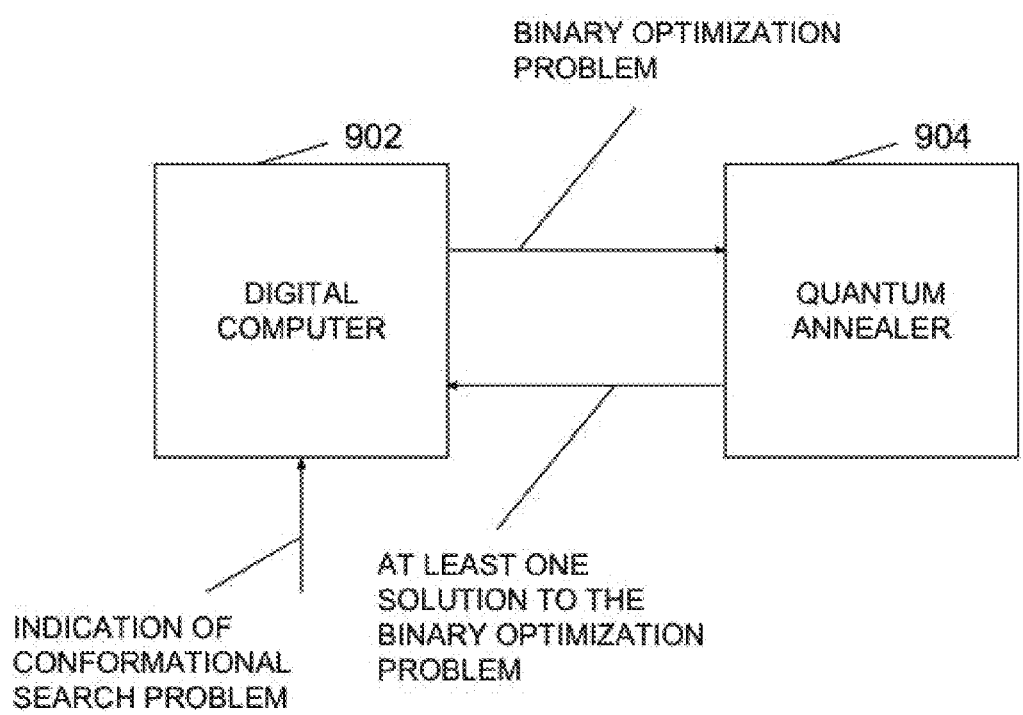
FIG. 9 is a diagram which shows an embodiment of a system in which the method for determining a conformation of a molecule using a high-performance binary optimizer may be implemented. In this specific embodiment, the system comprises a digital computer and a quantum annealer.

Now referring to FIG. 9, there is shown an embodiment of a system 900 in which the method for determining a conformation of a molecule using a high-performance binary optimizer may be implemented. In this specific embodiment, the high-performance binary optimizer is a quantum annealer 904. The quantum annealer 904 is operatively connected to a digital computer 902. The skilled addressee will appreciate that the digital computer 902 may be of various types. In one embodiment, the digital computer 902 is selected from a group consisting of desktop computers, laptop computers, tablet PC's, servers, smartphones, etc. It will also be appreciated that, in the foregoing, the digital computer 902 may also be broadly referred to as a processor. The skilled addressee will also appreciate that the digital computer 902 may be operatively connected to the quantum annealer 904 according to various embodiments known to the skilled addressee.

More precisely and in accordance with an embodiment, the digital computer 902 comprises a central processing unit, also referred to as a microprocessor, input/output devices, a display device, communication ports, a data bus and a memory unit. It will be appreciated that the central processing unit, the input/output devices, the display device, the communication ports and the memory unit are operatively coupled using the data bus.

The central processing unit is used for processing computer instructions. The skilled addressee will appreciate that various embodiments of the central processing unit may be provided.

The input/output devices are used for inputting/outputting data into the digital computer 902.

The display device is used for displaying data to a user. The skilled addressee will appreciate that various types of display device may be used.

The communication ports are used for operatively connecting for instance the digital computer 902 to the quantum annealer 904.

The communication ports may comprise, for instance, universal serial bus (USB) ports for connecting a keyboard and a mouse to the digital computer 902.

The communication ports may further comprise a data network communication port such as an IEEE 802.3.

The skilled addressee will appreciate that various alternative embodiments of the communication ports may be provided.

The memory unit is used for storing computer-executable instructions.

The memory unit may comprise a system memory such as a high-speed random access memory (RAM) for storing system control program (e.g., BIOS, operating system module, applications, etc.) and a read-only memory (ROM).

It will be appreciated that the memory unit comprises, in one embodiment, an operating system (OS) module.

It will be appreciated that the operating system module may be of various types. The operating system may be any member of the group consisting of: batch OS, multitasking/time sharing OS, multiprocessing OS, real time OS, distributed OS, network OS and mobile OS. Some of commercially available operating systems are Windows™, mac OS™ and Linux™.

The memory unit further comprises an application for determining a conformation of a molecule on at least one degree of freedom to optimize according to a molecular objective function using a high-performance binary optimizer characterized by at least one property.

More precisely, the application for determining a conformation of a molecule comprises instructions for providing an indication of a conformational search problem comprising an indication of a molecule comprising a plurality of atoms and at least one corresponding degree of freedom to optimize and a corresponding molecular objective function.

The application for determining a conformation of a molecule further comprises instructions for generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize.

The application for determining a conformation of a molecule further comprises instructions for generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize.

The application for determining a conformation of a molecule further comprises instructions for generating at least one neighborhood using the generated data structure and the at least one property of the high-performance binary optimizer, wherein the generating of a given neighborhood comprises restricting at least one data of the second set of data of the data structure to at least one given value.

The application for determining a conformation of a molecule further comprises instructions for, for each generated neighborhood of the at least one generated neighborhoods: generating a corresponding binary optimization problem using the data structure having the at least one data of the second set of data restricted to the at least one given value and the corresponding molecular objective function, providing the generated corresponding binary optimization problem to the high-performance binary optimizer, obtaining at least one solution from the high-performance binary optimizer.

The application for determining a conformation of a molecule further comprises instructions for providing at least one corresponding solution.

Describing the details of processing step 100, in one embodiment of processing step 300, the indication of the molecule to be optimized is provided using a file, for example with a .mol or .sdf file. Such file contains the information about the atoms' positions as well as the bonds connecting them.

In one embodiment, the optimization is limited to the torsional degrees of freedom of the molecule. For this, the user inputs all or a subset of the rotatable bonds of the molecule according to processing step 302 as an indication of the degrees of freedom to be optimized. In another embodiment, the rotatable bonds are inferred based on the molecular structure. The number of selected torsion bonds is denoted by M. The ith rotatable bond is denoted by $T_i$ and a variable $t_i$ is assigned to the rotational angle around $T_i$ with i being the torsion index. Having the indication of the molecule, an arbitrary conformation of the molecule can be represented by a vector $t=[t_1, t_2, \ldots, t_M]$, called the torsion angles vector.

In one embodiment, each torsion angle takes on values from a finite set of discrete angle values. Each set can be different for various torsion angles. In a related embodiment, all torsion angles take on values from the same set, containing d angle values. This set is denoted by $\Theta$ in the following.

In one embodiment, the objective function, input by user at processing step 304, is a molecular energy function. In one embodiment, the energy function is the Lennard-Jones 6-12 type potential that models the interaction energy of atoms $\alpha$ and $\beta$ as:

$$V(\alpha, \beta) = \epsilon_{\alpha\beta}\left[\left(\frac{\sigma_{\alpha\beta}}{r_{\alpha\beta}}\right)^{12} - 2\left(\frac{\sigma_{\alpha\beta}}{r_{\alpha\beta}}\right)^{6}\right],$$

wherein $\epsilon_{\alpha\beta}$ is the depth of the potential well, $\sigma_{\alpha\beta}$ is the van der Waals bond length, and $r_{\alpha\beta}$ is the distance between the two atoms. The skilled addressee will recognize this widely used energy model as well as alternative choices.

In a related embodiment, the interaction energy of two rigid bodies is defined as the summation of the energy of all pairs of atoms where the first atom in each pair belongs to the first rigid body and the second atom in each pair belongs to the second rigid body, wherein the interaction energy is specified by a given energy model.

Regarding processing step 102, in one embodiment wherein the high-performance binary optimizer is a quantum annealer, the number of registers and their connectivity pattern are obtained. The registers of this high-performance binary optimizer are qubits. In another embodiment, wherein the high-performance binary optimizer is the Fujitsu digital annealer, the number of bits is obtained and their connectivity is assumed to be complete, meaning that any of the bits are connected to all other bits. It will be appreciated that each register of the high-performance binary optimizer corresponds to a binary variable of the quadratic unconstrained binary optimization problem.

Regarding the details of processing step 104, in one embodiment of processing step 400, atoms of the molecule are partitioned into M+1 rigid bodies. The relative positions of the atoms within each rigid body are independent of the selected M torsional degrees of freedom.

In an embodiment of processing step 402, the rigid bodies graph of the molecule, denoted by $G=(\mathcal{R}, \mathcal{T})$, is generated where $\mathcal{R}$ is a set of M+1 vertices and $\mathcal{T}$ is a set of M edges. In G, each vertex represents a rigid body and each edge represents a rotatable bond and a corresponding rotational degree of freedom. Two vertices are connected by an edge if their associated rigid bodies are connected by the rotatable bond that the edge represents. In the following, $T_i$ is used to refer to both torsion i as well as its associated edge in the rigid bodies graph.

In one embodiment, it is assumed that each torsion bond is free to rotate independently of others, thus restricting the presence of ring systems or other cycles in the molecular graph to within individual rigid bodies. Under this assumption the rigid bodies graph has no cycles and is a tree.

In one embodiment of processing step 108, the initial conformation of the molecule is generated by choosing random values for the M torsion angles from their allowed set of discrete points and then rotating the atoms around the torsion bonds by the selected values. This initial conformation of the molecule may be represented by a torsion vector $t_{init}$.

In a related embodiment, the partially optimized conformation of the molecule is represented by a torsion vector, named $t_c$. At processing step 108, $t_c$ is also initialized by setting it equal to $t_{init}$. The molecular energy associated with the torsion vector $t_c$ is calculated based on the molecular objective function provided at processing step 304 and is named $E_c$.

Regarding details of processing step 110, in an embodiment of processing step 500 to select a neighborhood of $t_c$, the edges of the rigid bodies graph are contracted according to a neighborhood selection strategy. It will be appreciated that the set of the remaining edges after the contractions is said to be 2-torsion dependent if the resulting minor graph of G is a star graph. The maximal 2-torsion-dependent subsets of $\mathcal{T}$ are labeled by $\mathcal{T}_1, \ldots, \mathcal{T}_K$ while their associated star graphs are denoted by $G_1, \ldots, G_K$. Then, the neighborhood structure $N_k$ contains all solutions which only differ in torsion angle values corresponding to edges in $\mathcal{T}_k$ for $k=1, \ldots, K$, which are essentially the torsions to be optimized at processing step 504.

In a related embodiment, the neighborhood selection strategy is specified by an ordering of the torsion bonds where the selection of the edges for contraction on the rigid bodies graph follows this ordering. The ordering may be selected fully at random or according to some prior knowledge about the molecule.

In another embodiment of processing step 500, to account for the limit on the size of a complete quadratic unconstrained binary optimization problem that can be solved on the high-performance binary optimizer, a subset of $\Theta$ for each torsion in $\mathcal{T}_k$ is chosen. More specifically, if the size of the largest complete quadratic unconstrained binary optimization problem that can be solved on the high-performance binary optimizer is denoted by s, for each $T_i$ in $\mathcal{T}_k$, a set of $\Theta_i \subseteq \Theta$ discrete values are selected such that $\Sigma_{i:T_i \in \mathcal{T}_k} |\Theta_i| \leq s$.

In one embodiment where the high-performance binary optimizer is a quantum annealer, s is equal to the size of the largest complete quadratic unconstrained binary optimization problem that may be embedded on the quantum chip given its number of qubits and their connectivity pattern.

In a related embodiment, the $N_k$ neighborhood of $t_c$, denoted by $N_k(t_c)$, is defined as the set of torsion angle vectors t' that are different from $t_c$ only in the angle values of the torsions in $\mathcal{T}$. In addition, for any $T_i$ in $\mathcal{T}$, $t'_i$ (i.e. the value associated with $T_i$ in t') takes on values only from $\Theta_i$.

In an embodiment of processing step 502, a one-hot encoding is used for mapping the selected discrete points for torsions in $\mathcal{T}$ to the binary domain. For this purpose, a binary variables $x_{i\Theta_i}$ is assigned to a selected value $\theta_i \in \Theta_i$ for each $T_i$ in $\mathcal{T}$. To make sure that $T_i$ takes only one value at a time, the following constraint, called the one-hot encoding constraint, should be satisfied $$\sum_{\theta_i \in \Theta_i} x_{i\theta_i} = 1.$$

The above constraint should be satisfied for all torsions in $\mathcal{T}$.

In an embodiment of processing step 504, a binary optimization problem is formulated to optimize the partially optimized conformation over the neighborhood $N_k(t_c)$ selected at processing step 500.

In another embodiment of processing step 504, the problem of finding the best solution in $N_k(t)_c$ is formulated as a quadratic unconstrained binary optimization problem involving the binary variables corresponding to the torsions in $\mathcal{T}$ and moving the one-hot encoding constraints for all torsions in $\mathcal{T}$ to the objective function using the quadratic penalty method. The resulting quadratic unconstrained binary optimization problem is formulated as:

$$\min \sum_{\substack{i,j: T_i, T_j \in \mathcal{T}_k \\ i \neq j}} \sum_{\theta_i \in \Theta_i} \sum_{\theta_j \in \Theta_j} U_{ij}(\theta_i, \theta_j) x_{i\theta_i} x_{j\theta_j} +$$

$$\sum_{i: T_i \in \mathcal{T}_k} \sum_{\theta_i \in \Theta_i} U_i(\theta_i) x_{i\theta_i} + p \sum_{i: T_i \in \mathcal{T}_k} \left( \sum_{\theta_i \in \Theta_i} x_{i\theta_i} - 1 \right)^2$$

In the above equation, $U_{ij}(\theta_i, \theta_j)$ terms represent the interaction energy of the two vertices (rigid bodies) of $G_k$ that are connected by $T_i$ and $T_j$ when $t_i = \theta_i$ and $t_j = \theta_j$ and the rotation angle around all torsions not in $\mathcal{T}$ are set to their associated values in $t_c$. The $U_i(\theta_i)$ terms represent the interaction energy of the two vertices (rigid bodies) connected by $T_i$ on $G_k$ when $t_i=\theta_i$ the rotation angle around all torsions not in $\mathcal{T}$ are set to their corresponding values in $t_c$. Further, p is a sufficiently large penalty coefficient that enforces the one-hot encoding constraints.

In a related embodiment, $U_{ij}(\theta_i, \theta_j)$ in the above formulation is evaluated by a digital computer via applying rotation around $T_i$ and $T_j$, setting the rotation angle around torsions not in $\mathcal{T}$ to their values from the current $t_c$, and using the spatial arrangement of the molecule provided at processing step 300 to generate the new positions of the atoms. Having the new atoms' positions for the two rigid bodies connected by $T_i$ and $T_j$, their interaction energy is found using the energy model provided at processing step 304.

In an embodiment of processing step 506, the above quadratic unconstrained binary optimization problem is provided to the high-performance binary optimizer to be solved. It will be appreciated that this may be done according to various embodiments. It will be appreciated that the digital computer is operatively connected to a high-performance binary optimizer (HPBO). The connection may be of various types and is known to the skilled addressee. In one embodiment the digital computer is directly connected to the high-performance binary optimizer. In another embodiment, it is connected to the high-performance binary optimizer via a cloud connection.

In an embodiment of processing step 506, the quadratic unconstrained binary optimization problem is solved more than once by the high-performance binary optimizer in order to increase the chance of finding the optimal solution when the solutions returned by the high-performance binary optimizer have a probabilistic distribution. This applies to an embodiment wherein the high-performance binary optimizer is a quantum annealer as well as an embodiment wherein the high-performance binary optimizer is the Fujitsu Digital Annealer.

In an embodiment of processing step 508, the binary solution of the quadratic unconstrained binary optimization problem found by the high-performance binary optimizer is mapped to values for rotation around torsions in $\mathcal{T}$ based on the previously mentioned one-hot encoding. The torsion angles for the partially optimized conformation stored in $t_c$ are then replaced by these mapped values for any $T_i \in \mathcal{T}$. The updated $t_c$ is used in the next iteration of processing steps 500, 502, 504, 506, and 508 if the at least one stopping criterion is not met at processing step 510. The energy of the optimized conformation, $E_c$, is also updated according to the updated $t_c$.

In an embodiment of processing step 510, at least one stopping criterion is selected from a criteria list that comprises, in one embodiment, a criterion based on a total number of neighborhood selection and optimization in the torsional space, a criterion based on a total time spent on iterating over processing steps 500 to 508, and a criterion based on a threshold on a number of neighborhood optimizations that do not result in a meaningful decrease in $E_c$.

In an embodiment of processing step 512, the torsion vector $t_c$ as well as $E_c$ are used as the indication for the optimized conformation of the molecule and are passed to processing step 112.

In an embodiment of processing step 116, an indication of the collection of optimized conformations of the molecule is provided as one of a list that comprises a single file with a .sdf format and a plurality of files, e.g., multiple .mol files, wherein there is one file for each provided optimized conformation of the molecule.

Now referring to FIG. 2b, it will be appreciated that processing steps 100, 102, 104, and 106 are similar to what was disclosed for finding a collection of optimized conformations of the molecule using a quadratic unconstrained binary optimization problem solver, such as a quantum annealer or a Fujitsu Digital Annealer.

In an embodiment of processing step 200, a low-energy conformation of the molecule is found using a molecular energy optimization tool or some other prior knowledge of the molecule's energy.

It will be appreciated that processing steps 110 and 112 may be similar to what was disclosed previously for finding a collection of optimized conformations of the molecule using a quadratic unconstrained binary optimization problem solver.

In an embodiment of processing step 202, a test is performed on the size of the collection of found low-energy conformations of the molecule. If enough low-energy conformations of the molecule are collected, processing step 204 is performed, otherwise processing step 208 is performed.

In an embodiment of processing step 204, the optimized conformation of the molecule found at processing step 110 is compared with the already collected low-energy conformations of the molecule. If the optimized conformation of the molecule has a lower energy than the highest energy conformation in the collection of low-energy conformation of the molecule, processing step 206 is performed. Otherwise, processing step 210 is performed.

In an embodiment of processing step 206, the highest energy conformation of the molecule is removed from the collection of low-energy conformations of the molecule.

In one embodiment, before removing the highest energy conformation of the molecule from the collection of low-energy conformations of the molecule, molecular similarity, such as the values of the M torsion angles, between the optimized conformation of the molecule found at processing step 110 and the ones in the collection of low-energy conformations of the molecule are checked. If the optimized conformation of the molecule is not similar to any of them, or if it is similar to the highest energy conformation of the molecule in the collection, the highest energy conformation of the molecule is removed from the collection of low-energy conformations of the molecule.

In an embodiment of processing step 208, the energy-optimized conformation of the molecule found in processing step 110 is added to the collection of low-energy conformations of the molecule.

In an embodiment of processing step 210, at least one stopping criterion may be defined based on a target energy for the collected low-energy conformations of the molecule. That is, if one or some of the collected low-energy conformations of the molecule has a molecular energy not higher than a specific target energy, processing step 212 is performed. In one embodiment, this target energy is input by the user.

In an embodiment of processing step 212, an indication of the collection of low-energy conformations of the molecule is provided as one file, for example a file with an .sdf format, or using a plurality of files, e.g., multiple .mol files one for each low-energy conformation of the molecule.

It will be also appreciated that there is also disclosed a non-transitory computer-readable storage medium for storing computer-executable instructions which, when executed, cause a processing device to perform a method for determining a conformation of a molecule on at least one degree of freedom to optimize according to at least one molecular objective function using a high-performance binary optimizer characterized by at least one property, the method comprising providing an indication of a conformational search problem comprising an indication of a molecule comprising a plurality of atoms and at least one corresponding degree of freedom to optimize and a corresponding molecular objective function; generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize; generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize; generating at least one neighborhood using the generated data structure and the at least one property of the high-performance binary optimizer, wherein the generating of a given neighborhood comprises restricting at least one data of the second set of data of the data structure to at least one given value; for each generated neighborhood of the at least one generated neighborhoods, generating a corresponding binary optimization problem using the data structure having the at least one data of the second set of data restricted to the at least one given value and the corresponding molecular objective function, providing the generated corresponding binary optimization problem to the high-performance binary optimizer, obtaining a solution from the high-performance binary optimizer; and providing at least one corresponding solutions.

It will be appreciated that one of more embodiments of the method disclosed herein is of great advantage for various reasons.

More precisely, an advantage of one of more embodiments of the method disclosed is that it enables an efficient way to take advantage of high-performance binary optimizers to solve conformational search problems while addressing the exponential computational complexity of the problem.

Another advantage of one of more embodiments of the method disclosed is that it enables promising quantum technologies, such as quantum annealing, to be harnessed for solving problems of increasing complexity that are not possible to solve with traditional hardware on conventional CPUs.

Another advantage of one of more embodiments of the method disclosed is that it takes into account the limitations of high-performance binary optimizers and may be easily adapted to account for changing specifications and improvements of high-performance binary optimizers, thus providing a scalable method with evolving hardware.

Another advantage of one of more embodiments of the method disclosed is that it is flexible with the choice of degrees of freedom, molecular objective function, and possible restrictions to the values of the degrees of freedom to be optimized.

Another advantage of one of more embodiments of the method disclosed is that it may be combined with other solvers and methods for developing hybrid methods.

Another advantage of one of more embodiments of the method disclosed is that it may be used both for sampling high-quality conformations of the conformational search space and finding elite high-quality conformations.

The embodiments described above are intended to be exemplary only. The scope of the one or more embodiments of the invention is therefore intended to be limited solely by the appended claims.

The invention claimed is:

1. A computer-implemented method for determining a conformation of a molecule on at least one degree of freedom to optimize according to a molecular objective function using a binary optimizer characterized by at least one property and relying on digital annealing or quantum annealing, the method comprising:
   providing an indication of a conformational search problem comprising an indication of a molecule comprising a plurality of atoms and at least one corresponding degree of freedom to optimize and a corresponding molecular objective function;
   generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize;
   generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize;
   generating at least one neighborhood using the generated data structure and the at least one property of the binary optimizer, wherein the generating of a given neighborhood comprises restricting at least one data of the second set of data of the data structure to at least one given value;
   for each generated neighborhood of the at least one generated neighborhoods,
      generating a corresponding binary optimization problem using the data structure having the at least one data of the second set of data restricted to the at least one given value and the corresponding molecular objective function,
      providing the generated corresponding binary optimization problem to the binary optimizer,
      obtaining at least one solution from the binary optimizer;
      providing at least one corresponding solution; and
      applying at least one corresponding solution in drug discovery.

2. The computer-implemented method as claimed in claim 1, wherein the molecular objective function comprises one of a molecular energy model and a molecular surface area.

3. The computer-implemented method as claimed in claim 1, wherein the at least one degree of freedom is selected from a group consisting of a torsional degrees of freedom.

4. The computer-implemented method as claimed in claim 1, wherein the data structure is a rigid bodies graph comprising a plurality of vertices and at least one edge, further wherein each data of the first set of data is a corresponding vertex of the plurality of vertices of the rigid bodies graph and each data of the second set of data is an edge of the at least one edge of the rigid bodies graph.

5. The computer-implemented method as claimed in claim 1, wherein a plurality of corresponding binary optimization problems are generated for each generated neighborhood, further wherein each of the plurality of corresponding binary optimization problems generated is provided to the binary optimizer, further wherein a plurality of corresponding solutions are obtained from the binary optimizer.

6. The computer-implemented method as claimed in claim 5, further comprising selecting a solution amongst the plurality of corresponding solutions obtained for each neighborhood based on a criterion.

7. The computer-implemented method as claimed in claim 1, wherein the providing of a plurality of corresponding solutions comprises:
selecting at least one given solution based on a given criterion; and
providing the at least one selected solution.

8. The computer-implemented method as claimed in claim 1, wherein the indication of a conformational search problem further comprises at least one constraint associated with the conformational search problem, further wherein the at least one neighborhood is generated using the at least one constraint associated with the conformational search problem.

9. The computer-implemented method as claimed in claim 8, wherein the at least one constraint associated with the conformational search problem comprises a limitation on a value that a given degree of freedom to optimize may take.

10. The computer-implemented method as claimed in claim 9, wherein the value that a given degree of freedom to optimize may take is limited to one of at least one specific discrete value and a given range of values.

11. The computer-implemented method as claimed in any one of claim 1, wherein the indication of the conformational search problem comprises more than one corresponding molecular objective function.

12. The computer-implemented method as claimed in claim 1, wherein the obtaining of the at least one solution from the binary optimizer comprises receiving more than one solution for the generated corresponding binary optimization problem.

13. The computer-implemented method as claimed in claim 1, further comprising determining if a corresponding generated solution matches a criterion; further wherein the corresponding generated solution is discarded if it does not match the criterion.

14. The computer-implemented method as claimed in claim 13, wherein the criterion is selected from a group consisting of a maximum number of solutions to keep and a minimum corresponding quality for a solution defined according to the molecular objective function.

15. The computer-implemented method as claimed in claim 1, wherein the property of the binary optimizer comprises a maximum degree and connectivity of a binary polynomial optimization problem that can be solved by the binary optimizer.

16. The computer-implemented method as claimed in claim 1, wherein the binary optimizer is one of a quantum annealer and a digital annealer.

17. A non-transitory computer-readable storage medium for storing computer-executable instructions which, when executed, cause a processing device to perform a method for determining a conformation of a molecule on at least one degree of freedom to optimize according to a molecular objective function using a binary optimizer characterized by at least one property and relying on digital annealing or quantum annealing, the method comprising:
providing an indication of a conformational search problem comprising an indication of a molecule comprising a plurality of atoms and at least one corresponding degree of freedom to optimize and a corresponding molecular objective function;
generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize;
generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize;
generating at least one neighborhood using the generated data structure and the at least one property of the binary optimizer, wherein the generating of a given neighborhood comprises restricting at least one data of the second set of data of the data structure to at least one given value;
for each generated neighborhood of the at least one generated neighborhoods,
generating a corresponding binary optimization problem using the data structure having the at least one data of the second set of data restricted to the at least one given value and the corresponding molecular objective function,
providing the generated corresponding binary optimization problem to the binary optimizer,
obtaining at least one solution from the binary optimizer;
providing at least one corresponding solution; and
applying at least one corresponding solution in drug discovery.

18. A digital computing comprising:
a central processing unit;
a display device;
a communication port for operatively connecting the digital computer to a binary optimizer characterized by at least one property and relying on digital annealing or quantum annealing; and
a memory unit comprising an application for determining a conformation of a molecule on at least one degree of freedom to optimize according to a molecular objective function using the binary optimizer characterized by at least one property, the application comprising:
instructions for providing an indication of a conformational search problem comprising an indication of a molecule comprising a plurality of atoms and at least one corresponding degree of freedom to optimize and a corresponding molecular objective function;

instructions for generating using the at least one corresponding degree of freedom to optimize a connected rigid bodies representation for the molecule by identifying a plurality of groups of atoms, wherein each identified group of atoms is comprised of at least one atom, wherein each identified group that is comprised of at least two atoms is such that each atom of that corresponding given group of atoms remains at a position unchanged with respect to all other atoms of the given group of atoms for all possible values of the at least one degree of freedom to optimize;

instructions for generating a data structure representative of the connected rigid bodies representation using the connected rigid bodies representation, the data structure illustrating a relationship between a first set of data and a second set of data, wherein each data of the first set of data corresponds to a given group of atoms of the connected rigid bodies representation and each data of the second set of data corresponds to a degree of freedom to optimize;

instructions for generating at least one neighborhood using the generated data structure and the at least one property of the binary optimizer, wherein the generating of a given neighborhood comprises restricting at least one data of the second set of data of the data structure to at least one given value;

instructions for, for each generated neighborhood of the at least one generated neighborhoods:
  generating a corresponding binary optimization problem using the data structure having the at least one data of the second set of data restricted to the at least one given value and the corresponding molecular objective function, providing the generated corresponding binary optimization problem to the binary optimizer, and
  obtaining at least one solution from the binary optimizer;

instructions for providing at least one corresponding solution; and applying at least one corresponding solution in drug discovery.

* * * * *